(12) United States Patent
Kidane et al.

(10) Patent No.: US 7,759,359 B2
(45) Date of Patent: *Jul. 20, 2010

(54) METHOD OF TREATING BLADDER DYSFUNCTION WITH ONCE-A-DAY TROSPIUM SALT FORMULATION

(75) Inventors: Argaw Kidane, Montgomery Village, MD (US); Henry H. Flanner, Montgomery Village, MD (US); Padmanabh Bhatt, Rockville, MD (US); Arash Raoufinia, McLean, VA (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/889,964

(22) Filed: Aug. 17, 2007

(65) Prior Publication Data

US 2008/0207663 A1    Aug. 28, 2008

Related U.S. Application Data

(63) Continuation of application No. 10/980,818, filed on Nov. 4, 2004, now Pat. No. 7,410,978.

(60) Provisional application No. 60/517,198, filed on Nov. 4, 2003, provisional application No. 60/523,968, filed on Nov. 21, 2003.

(51) Int. Cl.
*A61K 31/44* (2006.01)
*A61K 31/40* (2006.01)

(52) U.S. Cl. ............ 514/299; 514/278; 514/279; 514/409; 514/410; 514/413; 514/414; 424/468

(58) Field of Classification Search ........ 514/278, 514/299; 424/468
See application file for complete search history.

(56) References Cited

U.S. PATENT DOCUMENTS

| | | | |
|---|---|---|---|
| 2,095,282 A | 10/1937 | Payne | |
| 2,956,926 A | 10/1960 | Greif | |
| 3,065,143 A | 11/1962 | Christenson | |
| 4,259,314 A | 3/1981 | Lowey | |
| 4,556,552 A | 12/1985 | Porter et al. | |
| 4,650,664 A | 3/1987 | Schepky et al. | |
| 4,668,684 A | 5/1987 | Tibes et al. | |
| 4,713,243 A | 12/1987 | Schiraldi et al. | |
| 4,828,836 A | 5/1989 | Elger et al. | |
| 4,871,548 A | 10/1989 | Edgren et al. | |
| 4,940,588 A | 7/1990 | Sparks et al. | |
| 5,158,777 A | 10/1992 | Abramowitz et al. | |
| 5,203,203 A | 4/1993 | Bryan et al. | |
| 5,242,927 A | 9/1993 | Baker et al. | |
| 5,273,760 A | 12/1993 | Oshlack | |
| 5,279,660 A | 1/1994 | Carlsson et al. | |
| 5,330,766 A | 7/1994 | Morella et al. | |
| 5,399,359 A | 3/1995 | Baichwal | |
| 5,405,648 A | 4/1995 | Hermann | |
| 5,455,047 A | 10/1995 | Bequette et al. | |
| 5,520,932 A | 5/1996 | McCurdy et al. | |
| 5,582,838 A | 12/1996 | Rork et al. | |
| 5,656,286 A | 8/1997 | Miranda et al. | |
| 5,686,094 A | 11/1997 | Acharya | |
| 5,837,285 A | 11/1998 | Nakamichi et al. | |
| 5,912,013 A | 6/1999 | Rudnic et al. | |
| 5,959,196 A | 9/1999 | Norcross, Jr. | |
| 5,962,024 A | 10/1999 | Marvola | |
| 5,972,389 A | 10/1999 | Shell et al. | |
| 5,998,430 A | 12/1999 | Schwantes et al. | |
| 6,004,582 A | 12/1999 | Faour et al. | |
| 6,024,976 A | 2/2000 | Miranda et al. | |
| 6,063,808 A | 5/2000 | Fabiano | |
| 6,141,625 A | 10/2000 | Smith et al. | |
| 6,156,340 A | 12/2000 | Adeyeye | |
| 6,197,331 B1 | 3/2001 | Lerner et al. | |
| 6,267,990 B1 | 7/2001 | Fischer et al. | |
| 6,312,726 B1 | 11/2001 | Nakamichi et al. | |
| 6,337,091 B1 | 1/2002 | Kim et al. | |
| 6,350,471 B1 | 2/2002 | Seth | |
| 6,375,985 B1 | 4/2002 | Bomberger et al. | |
| 6,437,000 B1 | 8/2002 | Mulye | |
| 6,534,091 B1 | 3/2003 | Garces Garces et al. | |
| 6,569,462 B1 | 5/2003 | Cornelli | |
| 6,632,451 B2 | 10/2003 | Penhasi et al. | |
| 6,635,680 B2 | 10/2003 | Mulye | |

(Continued)

FOREIGN PATENT DOCUMENTS

CA    2035155    10/1991

(Continued)

OTHER PUBLICATIONS

Reitz et al., European Urology, 2004, 45, 510-515.

(Continued)

*Primary Examiner*—Johann R Richter
*Assistant Examiner*—Nathan W Schlientz
(74) *Attorney, Agent, or Firm*—Arent Fox LLP.; Anna Ganelina

(57) ABSTRACT

A pharmaceutical composition of a pharmaceutically acceptable trospium salt, with upon administration to a human patient generates an average steady state blood levels of trospium with a minimum ($C_{min}$) and maximum ($C_{max}$) blood levels of about 0.5-2.5 ng/ml and about 2.0-6.0 ng/ml, respectively.

9 Claims, 11 Drawing Sheets

U.S. PATENT DOCUMENTS

| | | | |
|---|---|---|---|
| 6,638,528 | B1 | 10/2003 | Kanios |
| 6,645,528 | B1 | 11/2003 | Straub et al. |
| 6,652,837 | B1 | 11/2003 | Edwards et al. |
| 6,682,759 | B2 | 1/2004 | Lim et al. |
| 6,772,801 | B1 | 8/2004 | Shojaei et al. |
| 6,897,205 | B2 | 5/2005 | Beckert et al. |
| 6,905,709 | B2 | 6/2005 | Oshlack |
| 6,923,988 | B2 | 8/2005 | Patel et al. |
| 6,962,717 | B1 | 11/2005 | Huber et al. |
| 6,974,820 | B2 | 12/2005 | Aberg |
| 7,220,430 | B2 * | 5/2007 | Ishibashi et al. ............ 424/472 |
| 2002/0031550 | A1 | 3/2002 | Sauer |
| 2002/0047058 | A1 | 4/2002 | Verhoff et al. |
| 2002/0091099 | A1 | 7/2002 | Blackburn et al. |
| 2002/0110593 | A1 | 8/2002 | Penhasi et al. |
| 2003/0012815 | A1 | 1/2003 | Ishibashi et al. |
| 2003/0054032 | A1 | 3/2003 | Oshlack |
| 2003/0054041 | A1 | 3/2003 | Lemmens et al. |
| 2003/0064108 | A1 | 4/2003 | Lukas |
| 2003/0158176 | A1 | 8/2003 | Richards et al. |
| 2003/0185882 | A1 | 10/2003 | Vergez et al. |
| 2003/0199480 | A1 | 10/2003 | Haynes |
| 2004/0028729 | A1 | 2/2004 | Shojaei |
| 2004/0086571 | A1 | 5/2004 | Guivarc'h et al. |
| 2004/0091543 | A1 | 5/2004 | Bell et al. |
| 2004/0142035 | A1 | 7/2004 | Chang |
| 2004/0202693 | A1 | 10/2004 | Chang |
| 2004/0228917 | A1 | 11/2004 | Oshlack |
| 2005/0009862 | A1 | 1/2005 | Sabounjian |
| 2005/0043342 | A1 | 2/2005 | Aberg |
| 2006/0047007 | A1 | 3/2006 | Danehower |

FOREIGN PATENT DOCUMENTS

| | | |
|---|---|---|
| DE | 1194422 | 3/1963 |
| EP | 1101490 | 5/2001 |
| EP | 1125586 A1 | 8/2001 |
| GB | 1058542 | 2/1967 |
| WO | WO-00/12069 A1 | 3/2000 |
| WO | WO-00/27364 A1 | 5/2000 |
| WO | WO-01/15668 A1 | 3/2001 |
| WO | WO-01/62236 A2 | 8/2001 |
| WO | WO-0154671 A1 | 8/2001 |
| WO | WO-02/060415 A1 | 8/2002 |
| WO | WO 04/000280 A | 12/2003 |
| WO | WO 2004/625277 A | 7/2004 |
| WO | WO 2004/096125 A | 11/2004 |

OTHER PUBLICATIONS

Garely et al., Expert Opinion on Pharmacotherapy, 2002, 3(7), 827-833.

Junemann et al., Neurourology and Urodynamics, 1999, 18(4), 375-376.

Hofner et al., World J Urol, 2001, 19, 336-343.

Sigma Aldrich, online catalog, Hydroxypropyl methyl cellulose phthalate, Dec. 21, 2006.

Fusgen et al., Int J Clin Pharm Ther, 2000, 38(5), 223-234.

Schröder S, Jetter A, Zaigler M, Weyhenmeyer R, Krumbiegel G, Wächter W, Fuhr U, entitled "Trospium Chloride Absorption From The Human Gastrointestinal Tract Assessed By Local Enteral Adminstration," *Eur. J. Clin. Pharmacol.* (2002) 58, S97 (Poster demonstaration 4$^{th}$ Annual Congr,. On Clin. Pharmacol. Wiesbgasden, Nov. 2002).

Schröder S, Jetter A, Zaigler M, Weyhenmeyer R, Krumbiegel G, Wächter W, Fuhr U, entitled "Absorption pattern of trospium chloride along the human gastrointestinal tract assessed using local enteral administration," *International Journal of Clinical Pharmacology and Therapeutics*, vol. 42, No. 10 (2004), pp. 543-549.

Langguth P., et al., "Intestinal Absorption of the Quarternary Trospium Chloride: Permeability-Lowering factors and Bioavailabilities for Oral Dosage Forms"; European Journal of Pharmeaceutics and Biopharmaceutics, EL Sevier Science Publisher B.V., Amsterdam, NL, vol. 43, No. 3 Jun. 1997, pp. 264-272.

European Patent Office Supplementary Search Report mailed Jan. 22, 2008 in EP 04 08 0569.

Dmochowski, R.R. et al., "Advancements in Pharmacologic Management of the Overactive Bladder"; Urology 56 (Supplement 6A), Dec. 2000, Elsevier Science, Inc.

Breuel et al., Arzeimittelforschung 43(4): 461-4 (1993).

Friend, Oral Colon-specific Drug Delivery, CRC Press (1992), p. 63.

Froelich et al., Int. J. Clin. Pharmacol. Ther.: 40(7): 295-303 (2002).

Nugent et al., Gut 48:571-577 (2001).

Rodriguez et al., J. Controlled Release 55:67-77 (1998).

Washington et al., Physiological Pharmaceutics: Barriers to Drug Absorption, 2nd ed., CRC Press, 2001, p. 158.

Yamakita Biol. Pharm. Bul., 18 (10) 1409-1416 (1995).

Merck Index, 12th ed. pp. 397, 766, 1341, 1342, & 1667 (1996).

Leopold, Drug Targeting Organ Specific Strategies, Ch. 6, pp. 157-170 (2001).

Shojaei, "Systemic Drug Delivery via the Buccal Mucosal Route," Pharm. Tech. pp. 70-81 (2001).

Remington, 19th Edition, "Sustained Release Drug Delivery Systems" (Chapter 94) pp. 1660-1675, Mack Publishin Co., Easton, PA 1995.

Guo, "Pharmaceutical Applications of naturally occurring water-soluble polymers," Elsevier: Pharmaceutical Science & Technology Today, 1(6): 254-261 (1998).

Kennon, "Interaction Studies of Cationic Drugs with Anionic Polyelectrolytes-Sodium Carboxymethylcellulose," J. of Pharmaceutical Science 45 (3): 157-160 (1956).

Feely, Intern. J. of Pharm. 44 (1-3): 131-139 (1988).

Lapidus, J. of Pharma. Sci. 57(8): 1292-1301 (1968).

Office Action of Jun. 27, 2006, in U.S. Appl. No. 10/425,268.

Office Action of Jun. 18, 2007, in U.S. Appl. No. 10/425,268.

Office Action of Feb. 8, 2008, in U.S. Appl. No. 10/822,949.

Office Action of Aug. 1, 2008, in U.S. Appl. No. 10/822,949.

Office Action of Apr. 14, 2009, in U.S. Appl. No. 10/822,949.

Office Action of Aug. 14, 2009, in U.S. Appl. No. 10/822,949.

Office Action of Jan. 4, 2007, in U.S. Appl. No. 10/980,819.

Office Action of Jun. 22, 2007, in U.S. Appl. No. 10/980,819.

Office Action of Dec. 17, 2007, in U.S. Appl. No. 10/980,819.

Office Action of Oct. 3, 2008, in U.S. Appl. No. 10/980,819.

Office Action of May 15, 2009, in U.S. Appl. No. 10/980,819.

Office Action of Dec. 29, 2009, in U.S. Appl. No. 10/980,819.

Office Action of May 30, 2008, in U.S. Appl. No. 10/980,820.

Office Action of Dec. 2, 2008, in U.S. Appl. No. 10/980,820.

Office Action of Jun. 25, 2009, in U.S. Appl. No. 10/980,820.

Office Action of Oct. 13, 2009, in U.S. Appl. No. 10/980,820.

Office Action of Jan. 26, 2010, in U.S. Appl. No. 10/980,820.

Office Action of Oct. 22, 2007, in Canadian Patent Application No. 2,537,103.

Office Action of Jul. 8, 2008, in Canadian Patent Application No. 2,537,103.

Office Action of Feb. 3, 2009, in Canadian Patent Application No. 2,537,103.

Office Action of May 19, 2009, in Canadian Patent Application No. 2,537,103.

Office Action of Oct. 15, 2008, in European Patent Application No. 04 800 569.802123.

Office Action of Mar. 11, 2009, in European Patent Application No. 04 800 569.802123.

Summons to Attend Oral Argument of Nov. 3, 2009, in European Patent Application No. 04 800 569.802123.

Office Action of Aug. 11, 2009, in Mexican Application No. MX2008/060543.

Office Action of Jan. 13, 2009, in Mexican Application No. MX2008/060543.

Office Action of Jul. 14, 2008, in Mexican Application No. MX2008/060543.

Paddock Para IV Anda Notice letter to Allergan and Supernus Apr. 26, 2010.

Alloussi, S., et al., "Trospium chloride (Spasmo-lyt®) in patients with motor urge syndrome (detrusor instability): a double-blind, randomised, multicentre, placebo-controlled study", Journal of Drug Assessment, 1999, 2: 1-96; Brookwood Medical Publications, pp. 27-39.

de Boer, A.G. et al., "Rectal Drug Administration: Clinical Pharmacokinetic Considerations", Clinical Pharmacokinetics 7: 285-311 (1982), ADIS Press Australasia Pty Ltd.

van Hoogdalem, E.J., et al., "Pharmacokinetics of Rectal Drug Administration, Part I: General Considerations and Clinical Applications of Centrally Acting Drugs", Clin. Pharmacokinet. 21 (1): 11-26, 1991, Adis International Limited.

Physicians' Desk Reference 55 Edition 2001, 2600-2602.

Physicians' Desk Reference 56 Edition 2002, 2801-2803.

EPO Machine Translation of WO 2002/060415.

* cited by examiner

Dissolution of trospium chloride immediate release pellets in 0.1 N HCl media (pH 1.1).

Dissolution profiles for Trospium Chloride extended release pellets having various coating thickness.

Figure 3 Dissolution profiles for trospium chloride delayed release pellets (Eudragit L30D55)

METHOD OF TREATING BLADDER DYSFUNCTION WITH ONCE-A-DAY TROSPIUM SALT FORMULATION

CORRESPONDING RELATED APPLICATION

This application is a Continuation of U.S. application Ser. No. 10/980,818 filed Nov. 4, 2004 now U.S. Pat. No. 7,410,978, which claims the benefit under 35 U.S.C. §119(e) of U.S. Provisional Application No. 60/517,198 filed Nov. 4, 2003, and U.S. Provisional Application No. 60/523,968 filed Nov. 21, 2003, which are hereby incorporated by reference in their entirety.

FIELD OF THE INVENTION

The present invention is directed to pharmaceutical compositions that allow for once daily dosage forms of trospium. Trospium is indicated in the treatment of urinary frequency, urgency, nocturia, and urge-incontinence associated with detrusor instability, urge syndrome, and detrusor hyperreflexia. These compositions are useful in treating the aforementioned conditions with once-a-day administration.

BACKGROUND OF THE INVENTION

Trospium is a quaternary ammonium derivative of tropine, and has anticholinergic properties. The hydrophilicity of the molecule, due to its permanent positive charge, limits its lipid solubility. Trospium chloride has been shown to antagonize acetylcholine on excised strips of human bladder muscle. Antispasmodic activity has been shown in the bladder, the small intestine, and on contractility of the gall bladder. Trospium chloride exhibits parasympatholytic action by reducing smooth muscle tone, such as is found in the urogenital and gastrointestinal tracts. This mechanism enables the detrusor to relax, thus inhibiting the evacuation of the bladder. Lowering the maximum detrusor pressure results in improved adaptation of the detrusor to the contents of the bladder, which in turn leads to enhanced bladder compliance with increased bladder capacity.

Trospium chloride was introduced into the market as a spasmolytic agent in 1967 (German patent 1 194 422). Trospium chloride has been available in an orally administrable, solid administration form (tablets and dragees), for intravenous or intramuscular injection as a solution, and for rectal administration as suppositories, and is primarily used for the treatment of bladder dysfunctions (urge incontinence, detrusor hyperreflexia). The product has been on the market in Germany and several other European countries for a number of years for specific therapeutic indications including urinary frequency, urgency, nocturia, and urge-incontinence associated with detrusor instability, urge syndrome, and detrusor hyperreflexia.

Currently, in the European market there is an immediate release trospium chloride tablet (Spasmo-lyt®), which is indicated for the treatment of urge incontinence and detrusor hyperreflexia and is used as a 20 mg tablet taken twice daily or bid (a total dose of 40 mg per day). In common with other quaternary ammonium compounds, orally administered trospium chloride is slowly absorbed, with the maximum blood level achieved after 5-6 hrs. The oral bioavailability is approximately 10%, and is significantly reduced with the intake of high-fat food. There are side effects associated with the use of the twice-daily trospium chloride regimen, such as dry mouth, headache, constipation, dyspepsia, and abdominal pain. These side effects are associated with a high blood concentration of trospium chloride. Moreover, studies in which a 40 mg immediate release dose was given once daily resulted in higher overall incidence of adverse events as compared to 20 mg given twice daily.

A once-a-day administration of trospium is advantageous over the twice-a-day administration in terms of both patient compliance and reduced adverse events, thus providing better treatment of the conditions for which trospium chloride is indicated.

In order to provide for an effective once-a-day form of trospium, there is a need for unique formulation approaches that provide the desired therapeutic effects while minimizing, if not eliminating, the undesired side effects mentioned above. This means that the minimum blood trospium concentration ($C_{min}$) at steady state should be above the minimum therapeutically effective blood concentration and the maximum blood trospium concentration ($C_{max}$) also at steady state should be below the maximum toxic blood concentration over the treatment period. Trospium chloride and other quaternary ammonium compounds exhibit a limited window of absorption in the human gastrointestinal tract, presenting a significant challenge to formulating a once-a-day composition.

SUMMARY OF THE INVENTION

It is an object of the present invention to provide a pharmaceutical composition of any pharmaceutically acceptable trospium salt, typically trospium chloride, which can be given once a day yet meet the steady state blood levels required for the treatment or prevention of diseases or conditions that would benefit from its spasmolytic activity. Such a disease or condition includes, and the present invention is primarily directed to, such bladder dysfunctions as urge incontinence or detrusor hyperreflexia, nocturia, and urinary frequency.

Such once-daily compositions of a trospium salt are targeted to result in average steady state blood levels of trospium with a minimum ($C_{min}$) and maximum ($C_{max}$) blood levels of about 0.5-2.5 ng/ml and about 2.0-6.0 ng/ml, respectively, which blood levels have been shown to be safe and effective. Steady state blood levels preferably average between a $C_{min}$ of about 0.75 ng/ml and a $C_{max}$ of about 5.0 ng/ml, for dosage forms of the present invention that correspond to a 20 mg bid regimen.

In one aspect of the invention an extended release (XR) pharmaceutical composition is provided, which contains between about 25 mg and about 60 mg trospium chloride for once-a-day or qd administration, and which is characterized by having the following in vitro release profile in phosphate buffer (pH 7.5) dissolution medium: about 0-40% released in about 1 hour, about 20-85% released in about 4 hours and greater than 70% released in about 12 hours.

In yet another aspect of this invention a delayed release (DR) pharmaceutical composition is provided, which contains between about 25 mg and about 80 mg trospium chloride for once-a-day or qd administration, depending on the length of the lag phase. The in vivo delay in the release can be tailored to a particular application, but generally is from about 0.5 hour to about 6 hours, more preferably from about 2.5 hours to about 5 hours, during which time there should minimal, if any, detectable trospium in the blood. The in vitro release profile of such a formulation is generally characterized by having less than about 10% released in acidic media within 2 hours and more than about 80% released in buffer media of pH 6.8 and higher within 1 hour.

In still another aspect of the present invention an immediate release (IR) composition is provided, which contains no more than about 20 mg active drug, combined with a delayed release composition that is designed to dissolve at a pH of about 7.0 (i.e., in the lower part of the GI tract), such as the DR2 composition of the examples, to form a single once-a-day trospium chloride formulation containing in total about 80 mg drug.

Another aspect of the present invention is to provide a method for treating urinary frequency, urgency, nocturia, and urge-incontinence associated with detrusor instability, urge syndrome, and detrusor hyperreflexia with once-a-day administration of trospium chloride.

Yet another aspect of the invention provides a single dosage form that allows for an additional release, or pulse, of a drug with a short half-life at about the half-life ($t_{1/2}$) thereof. Such dosage forms are a significant challenge to develop when the drug is one, such as tropsium, that has a defined region of absorption in the upper GI tract, and is more poorly absorbed in the lower GI tract (i.e. the ileum area and colon).

The invention is also directed to a method of enteral administration of a pharmaceutical composition comprising an effective amount of a salt of trospium (e.g., trospium chloride), in which an improvement comprises including a delayed release formulation of said salt of trospium, which releases trospium at a pH of about 7.0. In another embodiment of the invention, a method is provided for an enteral administration of a pharmaceutical composition comprising an effective amount of a trospium salt (e.g., trospium chloride), in which an improvement comprises including a delayed release formulation of said trospium salt, which releases trospium in the lower intestine, preferably in the colon. Accordingly, the invention is further directed to a pharmaceutical composition comprising a trospium salt (preferably, trospium chloride) as at least one active pharmaceutical ingredient in which at least a portion of said trospium salt is contained in a delayed release formulation, which releases trospium at a pH of about 7.0. In an alternative embodiment, the invention is still further directed to a pharmaceutical composition comprising a trospium salt (preferably, trospium chloride) as at least one active pharmaceutical ingredient in which at least a portion of said trospium salt is contained in a delayed release formulation, which releases trospium in the lower intestine, colon, or both.

Finally, another aspect of the invention is to provide processes for preparing the once daily compositions of the present invention, and methods of treatment using them.

DETAILED DESCRIPTION OF THE INVENTION

Figure 1:
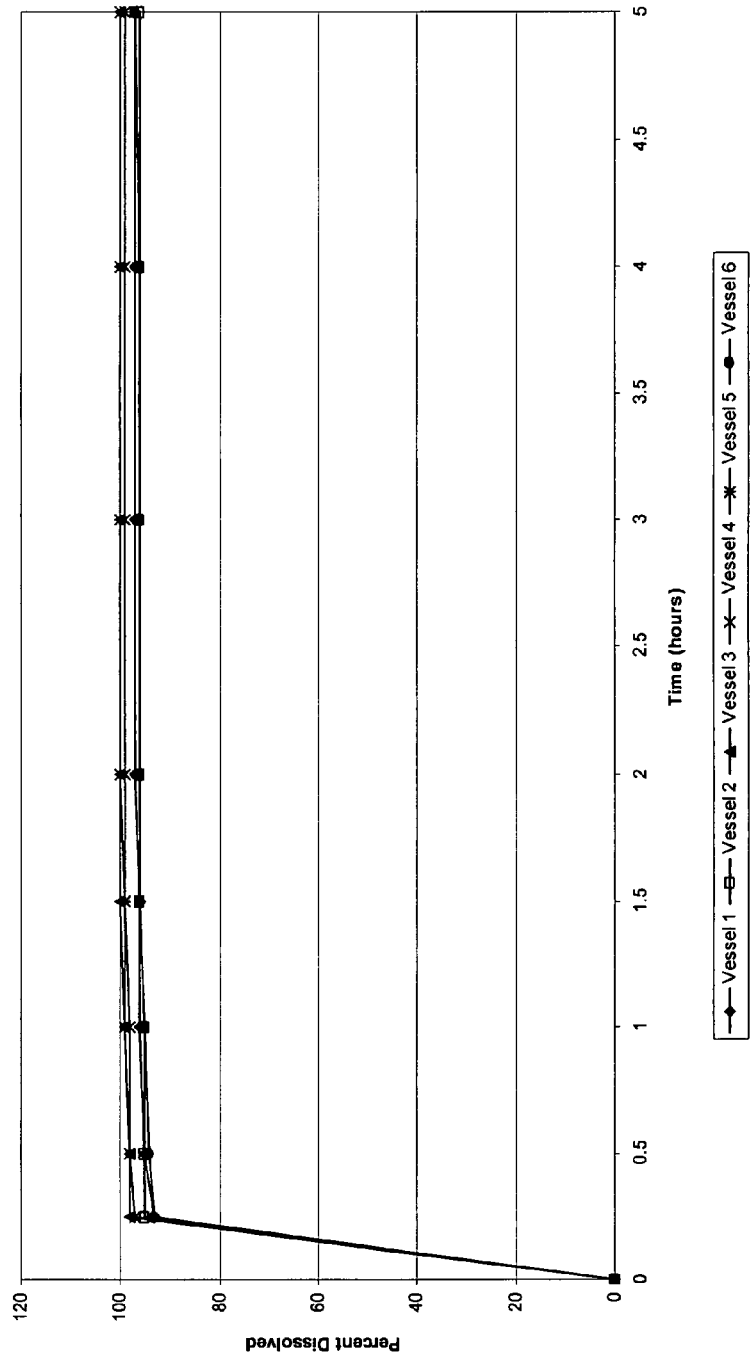
FIG. 1 shows the dissolution profiles for the immediate release trospium chloride pellets in 0.1N HCl, pH 1.1. The profiles show a release that reaches completion in about 15 minutes.

The present invention is primarily directed to once-daily, orally administrable forms of trospium, which due to its charged nature is usually found in the form of a salt, typically trospium chloride. Such formulations have not been previously known, most likely because trospium chloride presents challenges due to its high solubility and limited absorption window. Moreover, previous researchers have noted that due to the limited region of absorption, conventional modified release dosage forms were not thought practical. See, e.g., Schröder, S. et al. (Institute for Pharmacology, Clinical Pharmacology, University of K ln and Madaus AG, Köln, Germany). However, the present inventors have discovered oral dosage forms, which can be given once a day yet meet the steady state blood levels required for the treatment or prevention of diseases or conditions that would benefit from its spasmolytic activity.

The present invention is accomplished by providing an orally administered composition of trospium designed to provide certain steady state blood levels of the drug comparable to a twice-a-day regimen, preferably with some refinements, yet in a formulation that requires that the mammal, preferably human, take only one dosage a day. The preferred blood level of trospium is between about 0.5 and about 6.0 ng/ml at the steady state. Preferably, the blood levels stay within the preferred blood level, with once daily dosing, for the course of treatment. More preferably, the blood levels are between about 0.5 ng/ml and 5.0 ng/ml at the steady state. In addition, more preferably, a suitable once-a-day formulation exhibits a $C_{max}$ within 80 to 120% of the average $C_{max}$ of a corresponding twice-a-day formulation (typically one 20 mg IR twice a day, but could be titrated up or down) and a $C_{min}$ between 80 and 120% of the average $C_{min}$ of said twice daily regimen.

The concepts of the present invention may likewise be used to formulate controlled release compositions containing therapeutically active agents that exhibit similar solubility, limited absorption window and bioavailability characteristics as trospium. Examples of such compounds include, for instance, propantheline, emepronium, clidinium, and glycopyrrolate, which all are quaternary ammonium compounds.

As used herein, "about" means within the pharmaceutically acceptable limits found in the United States Pharmacopia (USP-NF 21), 2003 Annual Edition, or available at www.usp.org, for amount of active pharmaceutical ingredients. With respect to blood levels, "about" means within FDA acceptable guidelines.

The compositions of the present invention may be in the form of, among others, a granule, tablet (including matrix or osmotic), pellet, powder, sachet, capsule, gel, dispersion, solution or suspension. The only requirement is that the dosage forms be composed in such a manner as to achieve the profiles set forth herein.

In vivo profiles for trospium chloride that provide the appropriate blood (or, more particularly, plasma) concentration levels over time in order to meet the therapeutic requirements for once daily administration were determined in the present invention. The method used herein for the plasma concentration determination was the liquid chromatography/ mass spectrometry/mass spectrometry or LC/MS/MS method. With this technique, trospium is extracted from an aliquot of plasma using a solid phase extraction procedure. This extract is then analyzed using HPLC equipped with a mass spectrometer as a detector. These profiles are such that the mean blood trospium chloride levels provide an effective amount of the drug for the treatment of such conditions as urinary frequency, urgency, nocturia, and urge-incontinence due to detrusor instability, urge syndrome, and detrusor hyperreflexia, yet within such upper limits as to minimize the occurrence of adverse side effects typically associated with spikes in the plasma concentration that follow the multiple administration of immediate release formulations. The blood trospium chloride concentrations versus time profiles are characterized by a steady state $C_{min}$ of from about 0.5 to about 1.5 ng/ml, and a steady state $C_{max}$ of from about 2.0 to about 6.0 ng/ml.

With the present invention, it was surprisingly found that once daily dosing of trospium chloride in a delayed release formulation provides the required blood profile. Moreover, it was surprisingly found that once daily dosing with a dosage unit containing a combination of immediate release and delayed components provides a desired therapeutic blood profile. Still further, it was discovered that once daily dosing of trospium chloride in an extended release preparation also provides a desired therapeutically effective blood profile.

Thus, with the present invention it was found that an effective blood trospium chloride concentration at steady state could be achieved by formulating trospium chloride in several inventive ways. These dosage units are in the form of an extended release, a delayed release, or various combinations of immediate, extended and delayed release forms.

Immediate Release Composition

By "immediate release composition" is meant a dosage form that is formulated to release substantially all the active ingredient on administration with no enhanced, delayed or extended release effect. Such a composition for purposes of the present invention is, at least initially, in the form of a pellet (a term used interchangeably with "bead" or "beadlet" herein). The immediate release pellet can be one component of a plurality of components of a dosage form. The immediate release pellet can also serve as a precursor to an extended or delayed release pellet.

The non-active ingredients and processes for preparing such immediate release pellets are well known in the art, and the present invention is not limited in these respects. See, for example, Remington's Pharmaceutical Sciences, 18$^{th}$ Edition, A. Gennaro, Ed., Mack Pub. Co. (Easton, Pa. 1990), Chapters 88-91, the entireties of which are hereby incorporated by reference.

For instance, an immediate release pellet can be prepared by mixing the trospium salt (e.g., trospium chloride) with a bulking agent. Additionally, one can add disintegrating agents, antiadherants and glidants to the formulation.

Bulking agents employable in these compositions may be chosen from, among others: microcrystalline cellulose, for example, AVICEL® (FMC Corp.) or EMCOCEL® (Mendell Inc.), which also has binder properties; dicalcium phosphate, for example, EMCOMPRESS® (Mendell Inc.); calcium sulfate, for example, COMPACTROL® (Mendell Inc.); and starches, for example, Starch 1500; and polyethylene glycols (CARBOWAX®). Such bulking agents are typically present in the range of about 5% to about 75% (w/w), with a preferred range of about 25% to about 50% (w/w).

Suitable disintegrants include, but are not limited to: crosslinked sodium carboxymethyl cellulose (AC-DI-SOL®), sodium starch glycolate (EXPLOTAB® PRIMOJEL®) and crosslinked polyvinylpolypyrrolidone (Plasone-XL®). Disintegrants are used to facilitate disintegration of the pellet upon administration and are typically present in an amount of about 3% to about 15% (w/w), with a preferred range of about 5% to about 10% (w/w).

Antiadherants and glidants employable in such formulations can include talc, cornstarch, silicon dioxide, sodium lauryl sulfate, colloidal silica dioxide, and metallic stearates, among others.

In addition, the immediate release composition may contain one or more binders to give the pellets cohesiveness. Such binders are well known in the art, and include such substances as microcrystalline cellulose, polyvinyl pyrrolidone, starch, Maltrin, methylcellulose, hydroxypropyl methylcellulose, carboxymethyl cellulose, sucrose solution, dextrose solution, acacia, tragacanth and locust bean gum, which may be applied wet. The binding agent may be present in the composition in an amount of from about 0.2 wt % to about 20 wt %, preferably from about 5 wt % to about 15 wt %.

The pellets can be made by, for example, simple granulation such as wet granulation or dry granulation, followed by sieving; extrusion and marumerization (spheronization); rotogranulation; or any agglomeration process that results in a pellet of reasonable size and robustness. For extrusion and marumerization, the drug and other additives are granulated by addition of a binder solution. The wet mass is passed through an extruder equipped with a certain size screen, and the extrudates are spheronized in a marumerizer. The resulting pellets are dried and sieved for further applications.

One may also use high-shear granulation, wherein the drug and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications.

Alternatively, and preferably, the immediate release beadlets or pellets are prepared by solution or suspension layering, whereby a drug solution or dispersion, with or without a binder and optionally an anti-tacking agent such as talc, is sprayed onto a core or starting seed (either prepared or a commercially available product) in a fluid bed processor or other suitable equipment. The cores or starting seeds can be, for example, sugar spheres or spheres made from microcrystalline cellulose. The binder in the formula can be present in amounts ranging from about 0% to about 5% by weight, and preferably about 0.5% to about 2% by weight. The amount of anti-tacking agent used can be from about 0% to about 5%, preferably about 0.5% to about 2% by weight. The drug thus is coated on the surface of the starting seeds. The drug may also be layered onto the drug-containing pellets described above, if desired. Following drug layering, the resulting drug-loaded pellets are dried for further applications.

A protective layer, or overcoating, may be desired to ensure that the drug-loaded pellets do not aggregate during processing or upon storage. The protective coating layer may be applied immediately outside the core, either a drug-containing core or a drug-layered core, by conventional coating techniques such as pan coating or fluid bed coating using solutions of polymers in water or suitable organic solvents or by using aqueous polymer dispersions. OPADRY® (polyethylene glycols), OPADRY II® (Colorcon) and corresponding color and colorless grades from Colorcon can be used to protect the pellets from being tacky and provide colors to the product. The suggested levels of protective or color coating are from about 1% to about 6%, preferably about 2% to about 3% (w/w). Many ingredients can be incorporated into the overcoating formula, for example to provide a quicker immediate release, such as plasticizers: acetyltriethyl citrate, triethyl citrate, acetyltributyl citrate; dibutylsebacate, triacetin, polyethylene glycols, propylene glycol and the others; lubricants: talc, colloidal silica dioxide, magnesium stearate, calcium stearate, titanium dioxide, magnesium silicate, and the like.

The immediate release pellets are contemplated as being used in combination with extended release pellets and/or delayed release pellets in a single dosage form.

Extended Release Composition (XR)

Trospium chloride extended release pellets can be prepared, for example, by coating drug layered inert pellets with release controlling polymers. First, the inert pellet is coated with the drug layer or a drug loaded granule is prepared, as described above. Then the active (drug loaded) pellet is coated with a release controlling polymeric membrane. The release controlling coating layer may be applied immediately outside the core (such as a drug-containing core or a drug-layered core), by conventional coating techniques, such as pan coating or fluid bed coating, using solutions of polymers in water or suitable organic solvents or by using aqueous polymer dispersions. As an alternative embodiment, the release controlling membrane can separate additional drug layers on the core; for instance, after coating with the release controlling substance, another drug layer can be applied, which is followed by another release controlling layer, etc. Suitable materials for the release controlling layer include EUDRAGIT® RL (copolymers of acrylic and methacrylic acid esters), EUDRAGIT® RS (copolymers of acrylic and methacrylic acid esters), cellulose derivatives such as ethylcellulose aqueous dispersions (AQUACOAT®, SURELEASE®), hydroxyethyl cellulose, hydroxypropyl cellulose, hydroxypropyl methylcellulose, polyvinylpyrrolidone, polyvinylpyrrolidone/vinyl acetate copolymer, OPADRY®, and the like. The thickness of the coating affects the release profile, and so this parameter can be used to customize the profile. The suggested coating levels are from about 1% to about 40%, preferably about 5% to about 30% (w/w), and about 20% or about 25% as most preferred embodiments. A 20% w/w coating should release about 80% of the trospium chloride in 3.5 hours post ingestion, and a 25% w/w coating should result in the release of about 80% of the trospium chloride in 4.5 hours post-ingestion.

The extended release pellets contain between about 25 and about 60 mg trospium chloride, and may be used alone, or in combination with immediate release or delayed release pellets to constitute a single daily dosage form.

Delayed Release Composition (DR)

The delayed-release component has a coat applied to the surface of the active pellet that delays the release of the drug from the pellet after administration for a certain period of time. This delayed release is accomplished by applying a coating of enteric materials. "Enteric materials" are polymers that are substantially insoluble in the acidic environment of the stomach, but are predominantly soluble in intestinal fluids at various specific pHs. The enteric materials are non-toxic, pharmaceutically acceptable polymers, and include, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, carboxymethyl ethylcellulose, co-polymerized methacrylic acid/methacrylic acid methyl esters such as, for instance, materials known under the trade name EUDRAGIT®L12.5, L100, or EUDRAGIT®S12.5, S100, and several commercially available enteric dispersion systems (e.g., EUDRAGIT® L30D55, EUDRAGIT® FS30D, EUDRAGIT® L100-55, EUDRAGIT® S100 (Rohm Pharma), KOLLICOAT® MAE30D and 30DP (BASF), ESTACRYL® 30D (Eastman Chemical), AQUATERIC® and AQUACOAT® CPD30 (FMC)). The foregoing is a list of possible materials, but one of skill in the art would appreciate that there are other such materials that would meet the objectives of the present invention of providing for a delayed release profile including tailoring release based on the ambient pH environment, temporal considerations and other factors.

These coating materials can be employed in coating the surfaces in a range of from about 1.0% (w/w) to about 50% (w/w) of the pellet composition. Preferably, these coating materials are in the range of from about 20 percent to about 40 percent (w/w). The pellets may be coated in a fluidized bed apparatus or pan coating, for example, in a conventional manner.

With the enteric-coated pellets, there is no substantial release of trospium in the acidic stomach environment of below about pH 4.5. The trospium becomes available when the pH-sensitive enteric layer dissolves at a higher pH in the GI tract, after a certain delayed time, or after the unit passes through the stomach. The preferred delay time is in the range of about 0.5 to about 6 hours, but more preferable is about 0.5 to about 4 hours.

More particularly, preferred DR pellets are those that are coated with Eudragit® L30D-55 (which dissolves at about pH 5.5-6.0, i.e., in the upper intestines), and others that are coated with Eudragit FS30D (which dissolves at about pH 7.0, i.e. in the lower intestine and colon).

As a variation of this embodiment, the DR pellet contains layers of the trospium, separated by protective (XR) or release-controlling (DR) layers, optionally surrounded by an IR layer, which will result in a pulsed dose delivery; in other words, a combination of an IR or XR with a DR in the same pellet. Such a dosage form is made as an alternative way to meet the blood level requirements of the release profile of the present invention, which may be comparable to separate IR/XR and IR/DR pellets in the same capsule.

Preferably, the DR pellets are used in combination with XR pellets, but may also be used with IR pellets or a combination of all three.

Immediate Release (IR)/Delayed Release (DR) Dosage Units

Pulsatile drug release can be achieved through a combination of immediate release and delayed release components in a single dosage form. For instance, a combination of the immediate release (IR) pellets and delayed release (DR) pellets described herein can be employed. With this approach, pellets coated with enteric polymer (DR pellets) are combined with drug-coated pellets (IR pellets) to provide an immediate release followed by a pulsed release of trospium. Whereas the IR portion provides a fast rise in the plasma-time profile, the DR portion helps ensure that an effective plasma level is maintained over a longer period of time, preferably a 24 hour period.

The ratio between the immediate-release component and the delayed-release component can be used to adjust the in vitro drug release profile and in vivo blood concentration profile. Moreover, the profile can be manipulated by the properties of the delayed-release coating. By providing the desired drug release profiles according to the present invention, the compositions eliminate the need for a second dose for the day. Additionally, the total dose of trospium is preferably at or below 80 mg to avoid undesirable side effects but more than 30 mg to achieve the desired antispasmodic effect.

Immediate Release (IR)/Extended Release (XR) Dosage Units

As an alternative embodiment, the once-daily dosage unit may contain a combination of IR and XR pellets, in ratios designed to be substantially equivalent to a twice a day regimen, or otherwise provide a once-daily dosage form that will be safe and effective with minimized side effects.

The immediate release portion is designed to provide an effective plasma level at early time points. The extended release portion of the dosage form is designed to maintain the effective blood level throughout a 24-hour period, thus providing coverage for 24 hr. The IR portion provides about 20 mg or less of trospium to provide effective blood levels and yet avoid the side effects associated with spikes in the plasma profile. The extended release portion provides about 20 mg to about 60 mg of trospium chloride, more preferably from about 20 to about 40 mg in the extended release form.

Immediate Release (IR)/Delayed Release (DR)/Extended Release (XR) Dosage Units

Yet another embodiment of the present invention is a multiparticulate dosage form, which combines the three types of pellets. This type of dosage unit will provide multiple pulses of drug release, with the effect being a more or less sustained blood level of trospium within the acceptable range.

With this combination, the IR portion is designed to provide an effective blood level soon after ingestion, which is maintained by the DR and XR combinations. The DR portion provides an immediate release after a delay. The XR portion provides an extended release profile that maintains the effective blood level of trospium throughout the course of the day. The total dose of trospium in this composition is no greater than 80 mg, preferably 60 mg with the IR portion accounting for a maximum of about 20 mg of the total. The DR and XR portions account for 10 mg to 60 mg combined with ratios of XR to DR ranging form about 1:10 to about 10:1.

Delayed Release (DR)/Extended Release (XR) Dosage Units

Yet another embodiment of the present invention is a multiparticulate dosage form, which combines the extended release pellets with delayed release pellets. While the XR portion provides a sustained blood profile, the DR portion prevents the blood level form falling below the effective level at later time points. The XR is designed to provide between 10 mg to 40 mg, preferably between 20 mg to 40 mg, and more preferably 30 mg trospium chloride. The DR portion is preferably a longer delayed release with a delay of about 2-4 hrs and provides between 10 mg and 40 mg, preferably between 20 mg and 40 mg, and more preferably 30 mg trospium chloride.

Dosage Forms

As noted previously herein, the compositions of the present invention can be in a number of different forms, such as tablets, powders, suspensions, solutions, etc. The composition is preferably in pellet/beadlet form, which can be incorporated into hard gelatin or other kinds of capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other materials that impart good flow properties. A lubricant can also be added if desired, such as polyethylene glycol, leucine, glyceryl behenate, magnesium stearate or calcium stearate. The multiparticulate capsules are preferred because they provide an increased surface area as opposed to a tablet, which allows for better release profiles and thus bioavailability.

However, the pellets described above can be incorporated into a tablet, in particular by incorporation into a tablet matrix, which rapidly disperses the particles after ingestion. In order to incorporate these particles into such a tablet, a filler/binder must be used in the tableting process that will not allow the destruction of the pellets during the tableting process. Materials that are suitable for this purpose include, but are not limited to, microcrystalline cellulose (AVICEL®), soy polysaccharide (EMCOSOY®), pre-gelatinized starches (STARCH® 1500, NATIONAL® 1551), and polyethylene glycols (CARBOWAX®). These materials should be present in the range of about 5%-75% (w/w), and preferably between about 25%-50% (w/w).

In addition, disintegrants are added to the tablets in order to disperse the beads once the tablet is ingested. Suitable disintegrants include, but are not limited to: crosslinked sodium carboxymethyl cellulose (AC-DI-SOL®), sodium starch glycolate (EXPLOTAB®, PRIMOJEL®), and crosslinked polyvinylpolypyrrolidone (Plasone-XL). These materials should be present in the range of about 3%-15% (w/w), with a preferred range of about 5%-10% (w/w).

Lubricants are also added to assure proper tableting, and these can include, but are not limited to: magnesium stearate, calcium stearate, stearic acid, polyethylene glycol, leucine, glyceryl behenate, and hydrogenated vegetable oil. These lubricants should be present in amounts from about 0.1%-10% (w/w), with a preferred range of about 0.3%-3.0% (w/w).

Tablets are formed, for example, as follows. The pellets are introduced into a blender along with AVICEL®, disintegrants and lubricant, mixed for a set number of minutes to provide a homogeneous blend which is then put in the hopper of a tablet press with which tablets are compressed. The compression force used is adequate to form a tablet; however, it is not sufficient to fracture the beadlets or coatings.

A pharmaceutical formulation for the delivery of trospium chloride for the effective treatment of urinary frequency, urgency, nocturia, and urge-incontinence associated with detrusor instability, urge syndrome, and/or detrusor hyperreflexia in a human patient comprising an extended release composition that provides an extended release upon oral administration to said patient; and a pharmaceutical acceptable carrier; wherein the pharmaceutical formulation is sufficient to maintain an effective level of trospium chloride in the patient over the course of at least 12 hours without further administration of trospium chloride. The total dosage of trospium chloride may be about 30 mg to 70 mg producing in a human patient a plasma concentration versus time curve having an area under the curve of about 30,000 pg-Hr/ml to about 80,000 pg-Hr/ml. The plasma concentration may have a maximum concentration of about 1.5 ng/ml to about 6.0 ng/ml. The plasma concentration may have a minimum concentration of about 0.5 ng/ml to about 1.5 ng/ml. The maximum concentration of value of the said plasma concentration curve may be reached in about 3 to about 24 hours after oral administration.

A pharmaceutical formulation for the delivery of trospium chloride for the effective treatment of urinary frequency, urgency, nocturia, and urge-incontinence associated with detrusor instability, urge syndrome, and/or detrusor hyperreflexia in a human patient comprising an extended release composition that provides a delayed release upon oral administration to said patient; and a pharmaceutical acceptable carrier; wherein the pharmaceutical formulation is sufficient to maintain an effective level of trospium chloride in the patient over the course of at least 12 hours without further administration of trospium chloride. The total dosage of trospium chloride may be about 30 to 70 mg producing in a human patient a plasma concentration versus time curve having an area under the curve of about 30,000 pg/ml*hr 1 to about 80,000 pg/ml*hr. The plasma concentration may have a maximum concentration of about 1.5 ng/ml to about 6.0 ng/ml. The plasma concentration may have a minimum concentration of about 0.5 ng/ml to about 1.5 ng/ml. The maximum concentration of value of the said plasma concentration curve may be reached in about 3 to about 24 hours after oral administration.

A pharmaceutical formulation for the delivery of trospium chloride for the effective treatment of urinary frequency, urgency, nocturia, and urge-incontinence associated with detrusor instability, urge syndrome, and/or detrusor hyperreflexia in a human patient comprising an immediate release and/or an extended release composition that provides an immediate release and/or an extended release upon oral administration to said patient; a delayed release composition that provides delayed release upon oral administration to said patient; and a pharmaceutical acceptable carrier; wherein the pharmaceutical formulation is sufficient to maintain an effective level of trospium chloride in the patient over the course of at least 12 hours without further administration of trospium chloride, and a peak plasma concentration of the trospium chloride reached after release of said delayed release composition exceeds the peak plasma concentration previously reached after release of said immediate release composition or extended release composition. The total dosage of trospium chloride may be about 30 to 70 mg producing in a human patient a plasma concentration versus time curve having an area under the curve of about 30,000 pg/ml*hr to about 80,000 pg/ml*hr. The plasma concentration may have a maximum concentration of about 1.5 ng/ml to about 6.0 ng/ml. The plasma concentration may have a minimum concentration of about 0.5 ng/ml to about 1.5 ng/ml. The maximum concentration of value of the said plasma concentration curve may be reached in about 3 to about 24 hours after oral administration.

A once a day pharmaceutical formulation of trospium chloride comprising an immediate release or an extended release composition combined with a delayed release composition wherein the formulation composition contains sufficient trospium chloride to obtain a mean blood plasma trospium concentration in a human patient is about 500 pg/mL to about 800 pg/mL within about 1-3 hour of oral administration; A plasma concentration versus time of the said once a day formulation has an area under the curve of about 30,000 pg/ml*hr to about 80,000 pg/ml*hr. The maximum concentration of said plasma concentration curve is about 1.5 ng/mL to about 6.0 ng/mL. The $T_{max}$ is about 5 and about 6 hours. The total trospium chloride dose is about 30 mg to 80 mg per dose. The immediate release or the extended release composition has a release of trospium chloride equal to about 5% to about 20% of the total dose content within 2 hours as measured in an in vitro dissolution test using an USP Apparatus II at 50 RPM in 950 ml 50 mM phosphate buffer at a pH between 6.8 and 7.5 at 37° C. Said immediate release or an extended release composition combined with a delayed release composition may be in a single unit or in separate units. Said unit or units may be erodible matrix systems, coated systems, osmotic systems or combinations thereof.

The invention contemplates a pharmaceutical composition suitable for a once-a-day administration of trospium chloride comprising an amount of solid, trospium chloride-bearing particulates, each particulate including one or more trospium chloride-release-controlling substances, such that once-a-day administration of said pharmaceutical composition provides steady state (i.e., not single dose but after at least a few daily doses, or starting approximately between about 72 hours to about 120 hours of continuous once daily dosing) blood levels of trospium, which are substantially equivalent to steady state blood levels of trospium achieved with twice daily administration of the available 20 mg immediate release trospium chloride tablets, provided that said solid, trospium chloride-bearing particulates cannot comprise trospium chloride-release-controlling substances selected exclusively from immediate release substances.

In a preferred embodiment of the invention the once-a-day administration of the controlled release pharmaceutical composition provides steady state blood levels of trospium falling in the range of about 0.5 ng/ml to about 6.0 ng/ml, and preferably, for the dosage level corresponding to the 20 mg bid regimen of trospium chloride, falling in the range of about 0.75 ng/ml to about 3.0 ng/ml. It will be understood by clinicians and others skilled in the art that patients may be titrated up or down from the conventional 20 mg bid trospium chloride dosage, in which case the dosage units of the present invention would be correspondingly adjusted. The range of drug concentration in the formulations of the present invention accounts for such adjustments, it being understood that the preferred drug ranges roughly correspond to the typical 20 mg bid dosage regimen.

The invention is also contemplated to provide a pharmaceutical composition in which once-a-day administration provides steady state blood $C_{max}$ levels of trospium falling in the range of about 2.5 ng/ml to about 4.5 ng/ml and $C_{min}$ levels of trospium falling in the range of about 0.5 ng/ml to about 1.5 ng/ml. Moreover, the invention provides pharmaceutical compositions in which once-a-day administration provides steady state areas under the curve falling in the range of about 30 to about 60 ng/ml*hr, preferably, falling in the range of about 35 to about 45 ng/ml*hr.

In a particular embodiment of the invention, pharmaceutical compositions are provided in which once-a-day administration provides steady state %F (i.e., relative bioavailability) values falling in the range of about 80 to about 120, preferably, falling in the range of about 90 to about 110.

Hence, the invention contemplates that a wide selection of one or more trospium chloride-release-controlling substances is selected for inclusion in the solid, trospium chloride-bearing particulates, including, for example, one or more trospium chloride-release-controlling substances selected from substances that provide for immediate release, delayed release, extended release, or pH-sensitive release of trospium chloride, provided that if an immediate release substance is selected, then the pharmaceutical composition also includes one or more delayed release, extended release, pH-sensitive release substances or combinations thereof.

Specific embodiments, described in further detail in the examples, include but are not limited to formulations that are designated DR1, DR2, XR, XR1-1, XR1-2, XR1+DR2 and IR/DR2, to name a few.

The invention also contemplates a method of treating a mammal suffering from a condition that would benefit from a once daily administration of an effective amount of trospium chloride, comprising administering to a mammal in need thereof a once-a-day formulation comprising an effective amount of trospium chloride which provides steady state blood levels of trospium, which are substantially equivalent to steady state blood levels of trospium achieved with twice daily administration of 20 mg bid immediate release trospium chloride tablets (or a corresponding titrated dose) and which will lessen side effects. The invention now will be described in particularity with the following illustrative examples; however, the scope of the present invention is not intended to be, and shall not be, limited to the exemplified embodiments below.

This invention provides profiles that would make an acceptable once-a-day dosing regimen for trospium chloride. Trospium chloride is a highly water-soluble compound with a saturation solubility of 500 mg/ml. This invention overcomes the challenge imposed by highly water-soluble drugs as the active pharmaceutical ingredient in extended release preparations. Once-a-day dosing has a decided advantage over multiple dosing, increasing, for example, the rates of patient compliance. Also, once-a-day dosing with controlled release formulations reduces the side effects associated with spikes in the plasma concentration, which follow the multiple dose administration of immediate release formulations.

Thus, the present invention is also directed to methods of treating a mammal, preferably human, by administering once a day a composition according to the present invention, which will give average steady state blood levels of trospium of a minimum of about 0.5 ng/ml and a maximum of about 6.0 ng/ml, and preferably between about 0.75 and about 5.0 ng/ml. Any of the various compositions described in this application can accomplish those blood levels, an achievement not previously thought possible. Schröder, S. et al., vide supra.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Trospium Chloride Immediate Release Pellets

Trospium chloride immediate release (IR) pellets were manufactured by coating 30/35-mesh sugar spheres with trospium chloride from a coating dispersion consisting of trospium chloride, hydroxypropylmethylcellulose (HPMC E5, a binder), talc (an anti-tacking agent), and water in a Glatt's® GPCG-1 fluid bed coater. Table 1 provides the formula composition of trospium chloride IR capsules, as well as modified release compositions, and Table 2 sets forth the composition of the pellets. The drug layering dispersion is prepared by dissolving the HPMC E5 in water, dissolving the trospium chloride therein, then dispersing the talc, and stirring for 20 minutes. The resulting dispersion was stirred throughout the coating process to prevent settling of coating components. Coating parameters for Glatt's® GPCG-1 are given in Table 3. The pellets generated contained about 20% w/w of trospium chloride.

Figure 2:
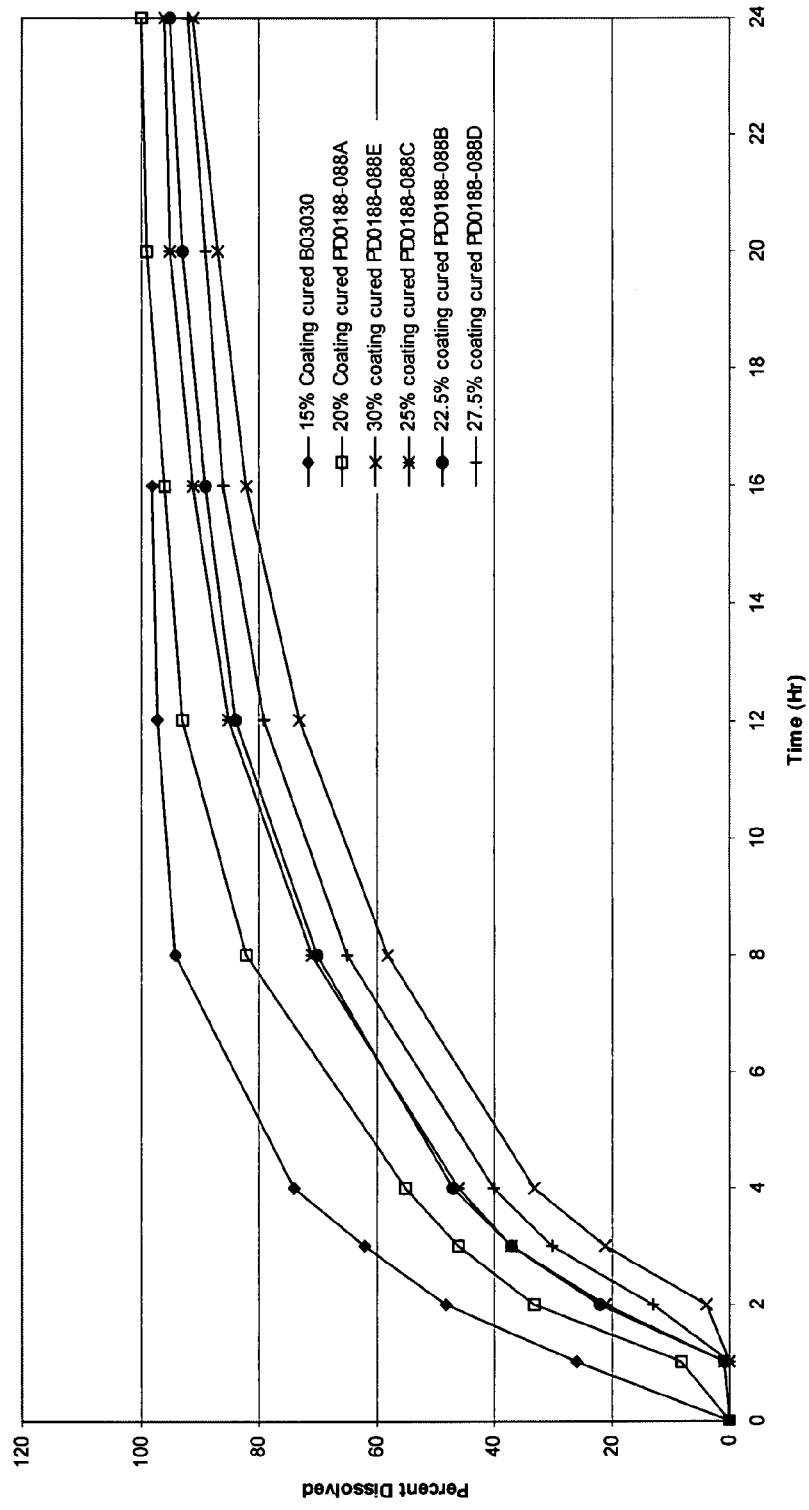
FIG. 2 shows the dissolution profiles for ethylcellulose coated (extended release or "XR") trospium pellets.
Figure 3:
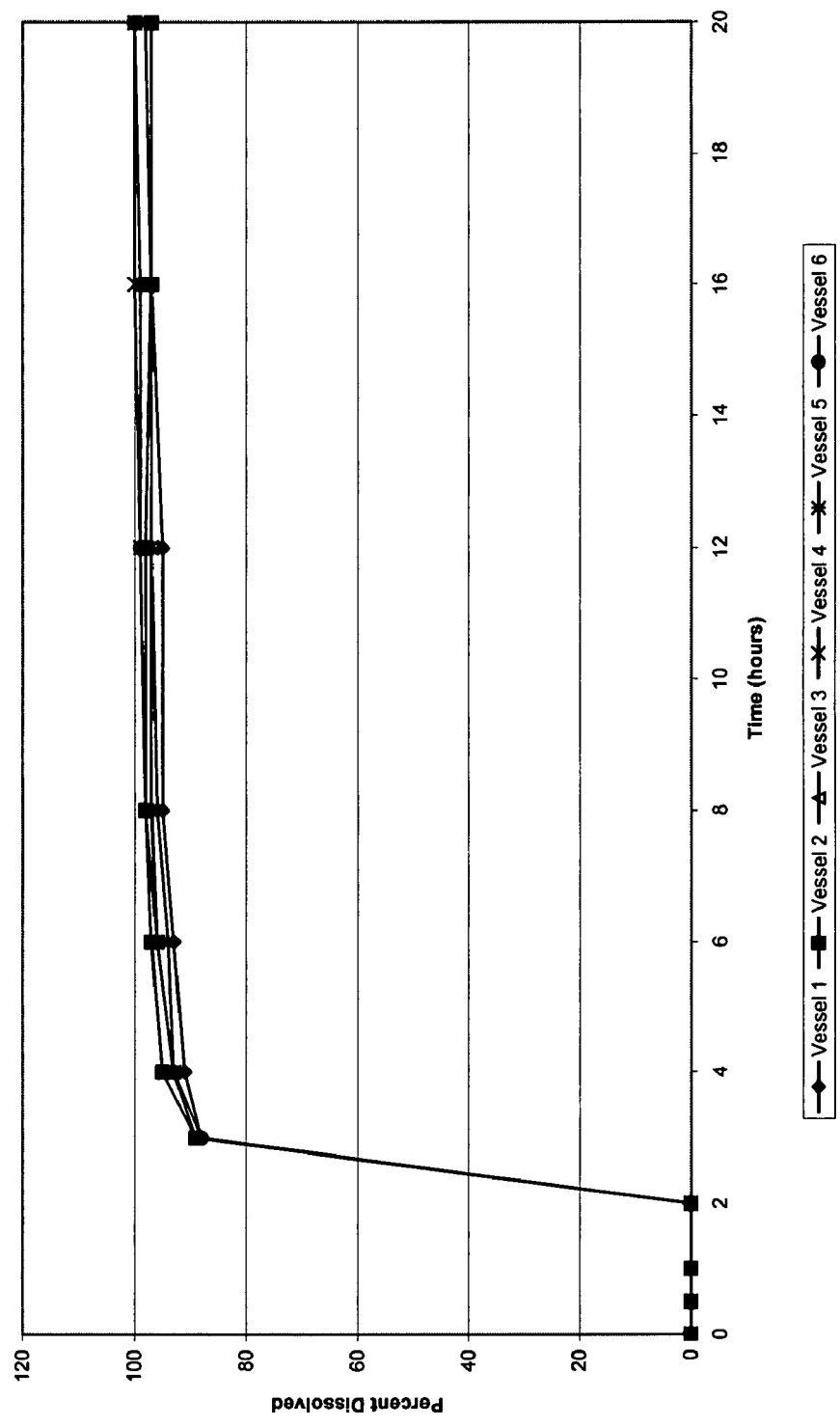
FIG. 3 shows the dissolution profiles for trospium chloride delayed release ("DR") pellets.
Figure 4:
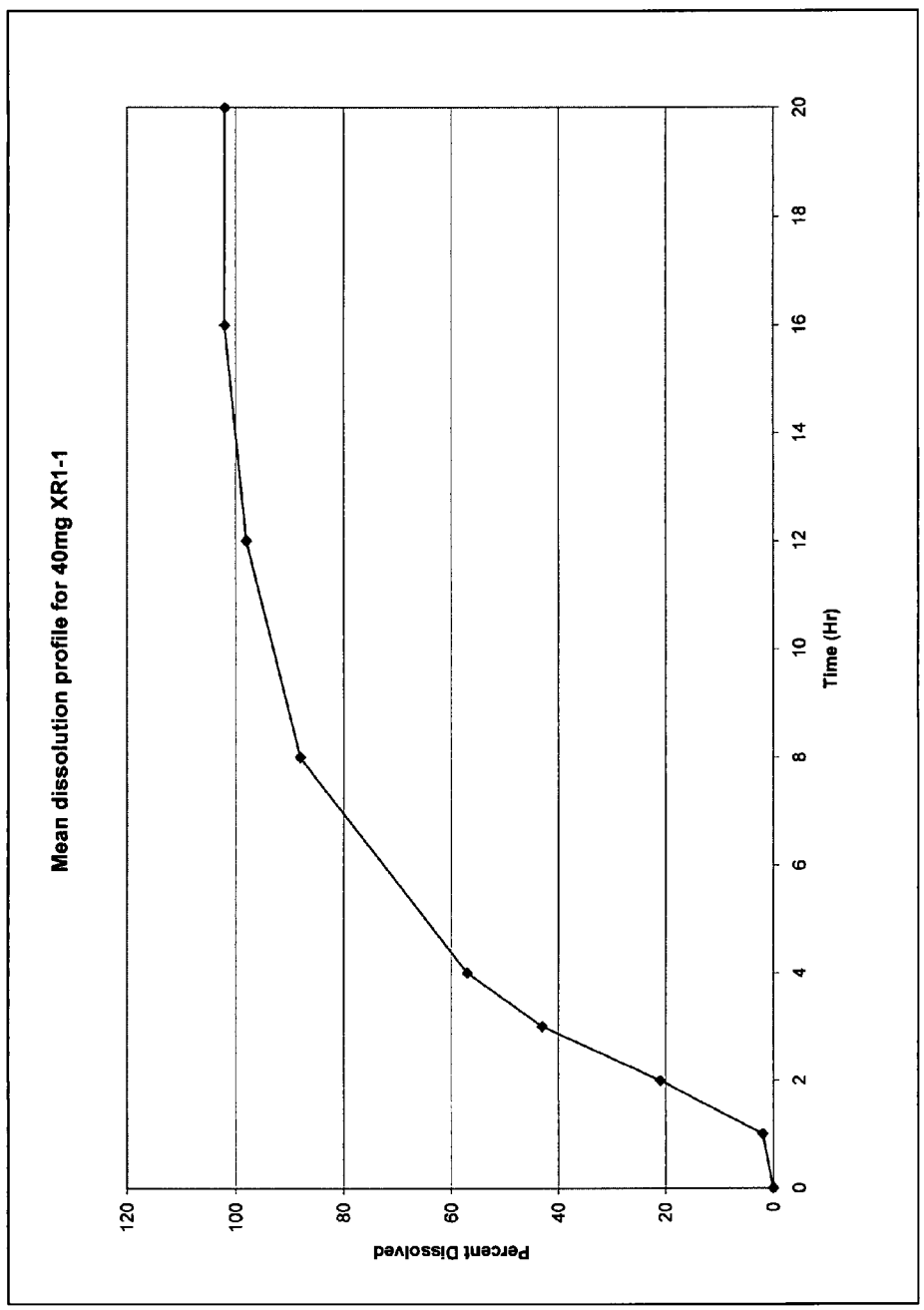
FIG. 4 shows the mean dissolution profile for 40 mg trospium chloride XR1-2 pellets.
Figure 5:
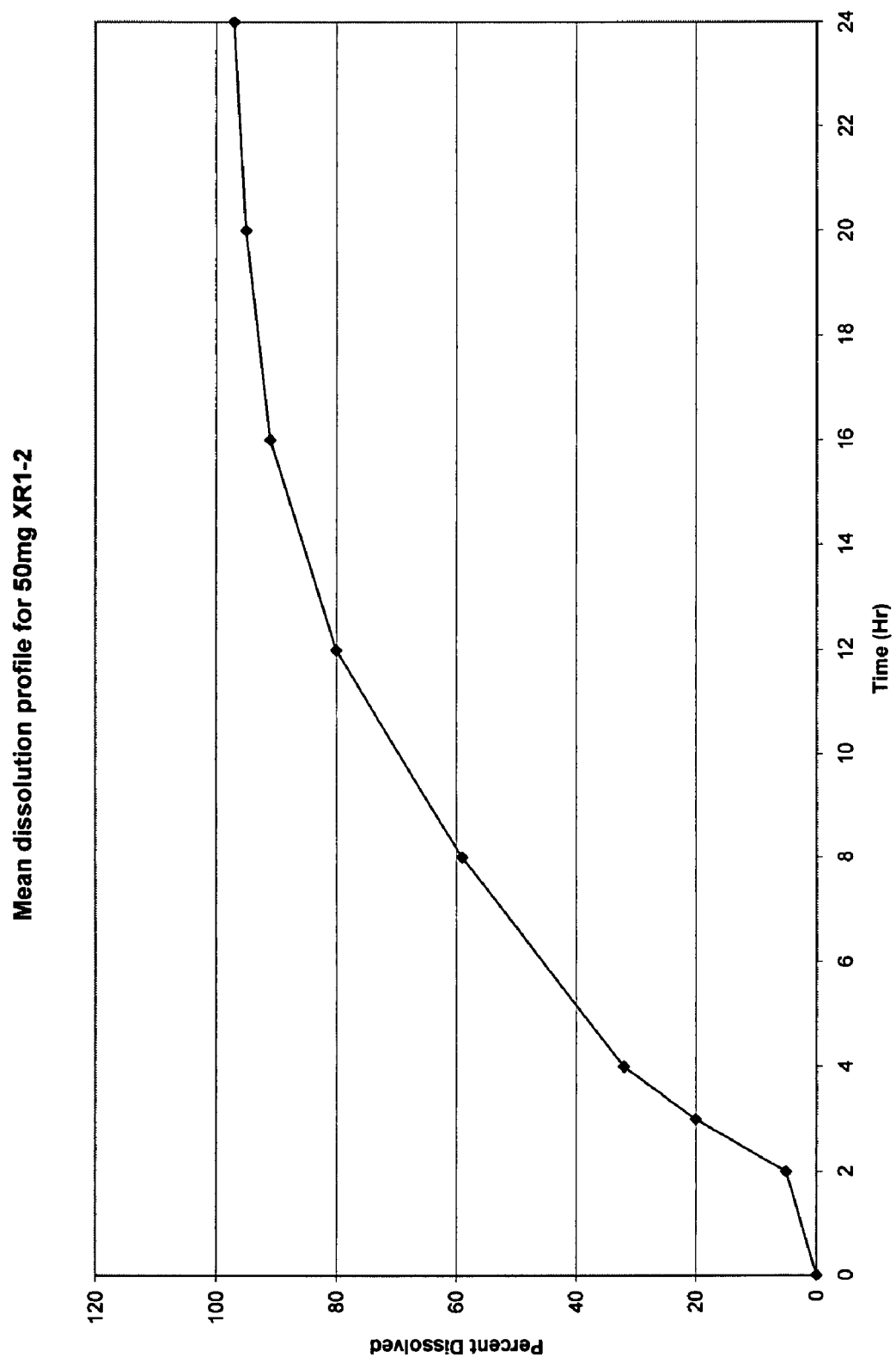
FIG. 5 shows the mean dissolution profile for 50 mg trospium chloride XR1-1 pellets.
Figure 6:
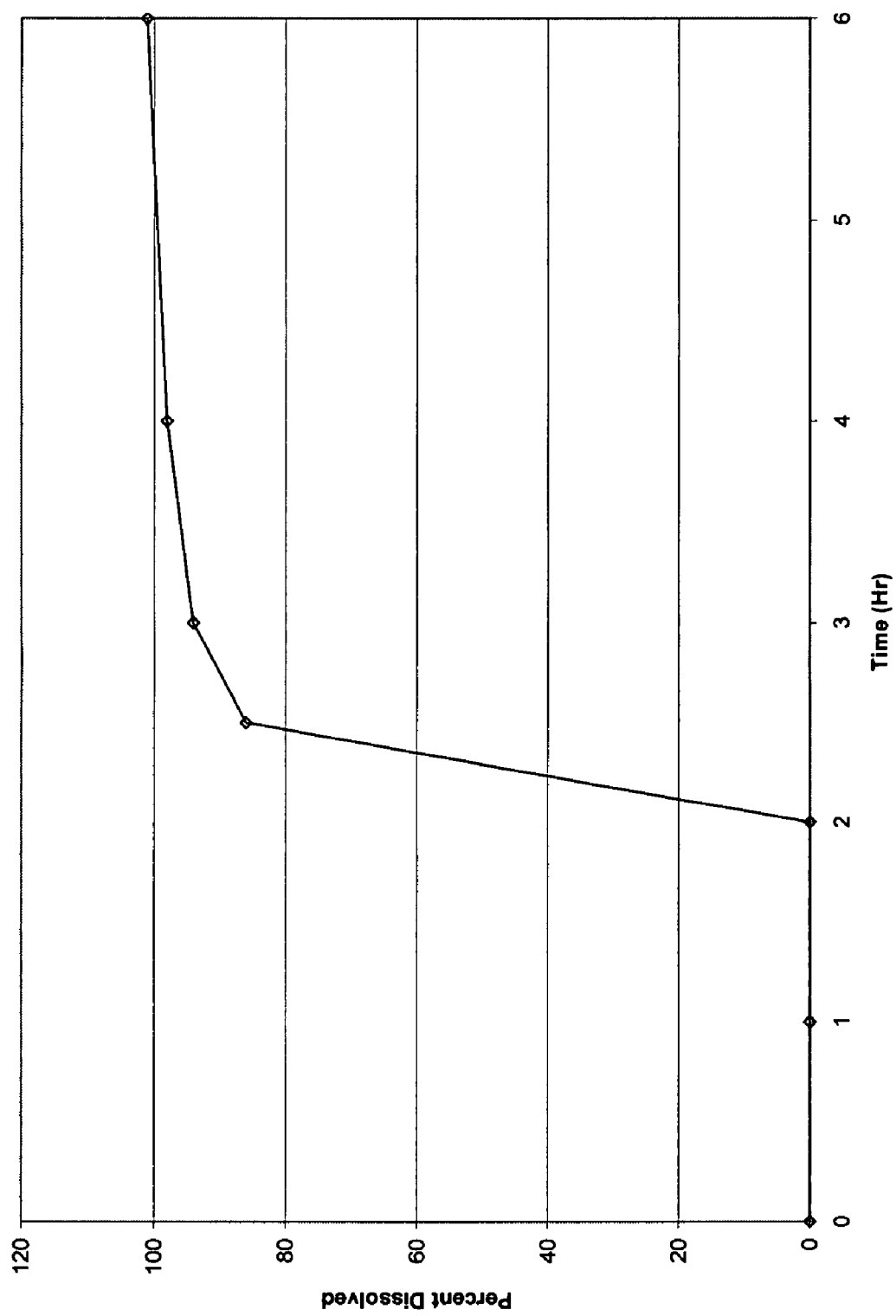
FIG. 6 shows the mean dissolution profile for 35 mg trospium chloride DR1 pellets.
Figure 7:
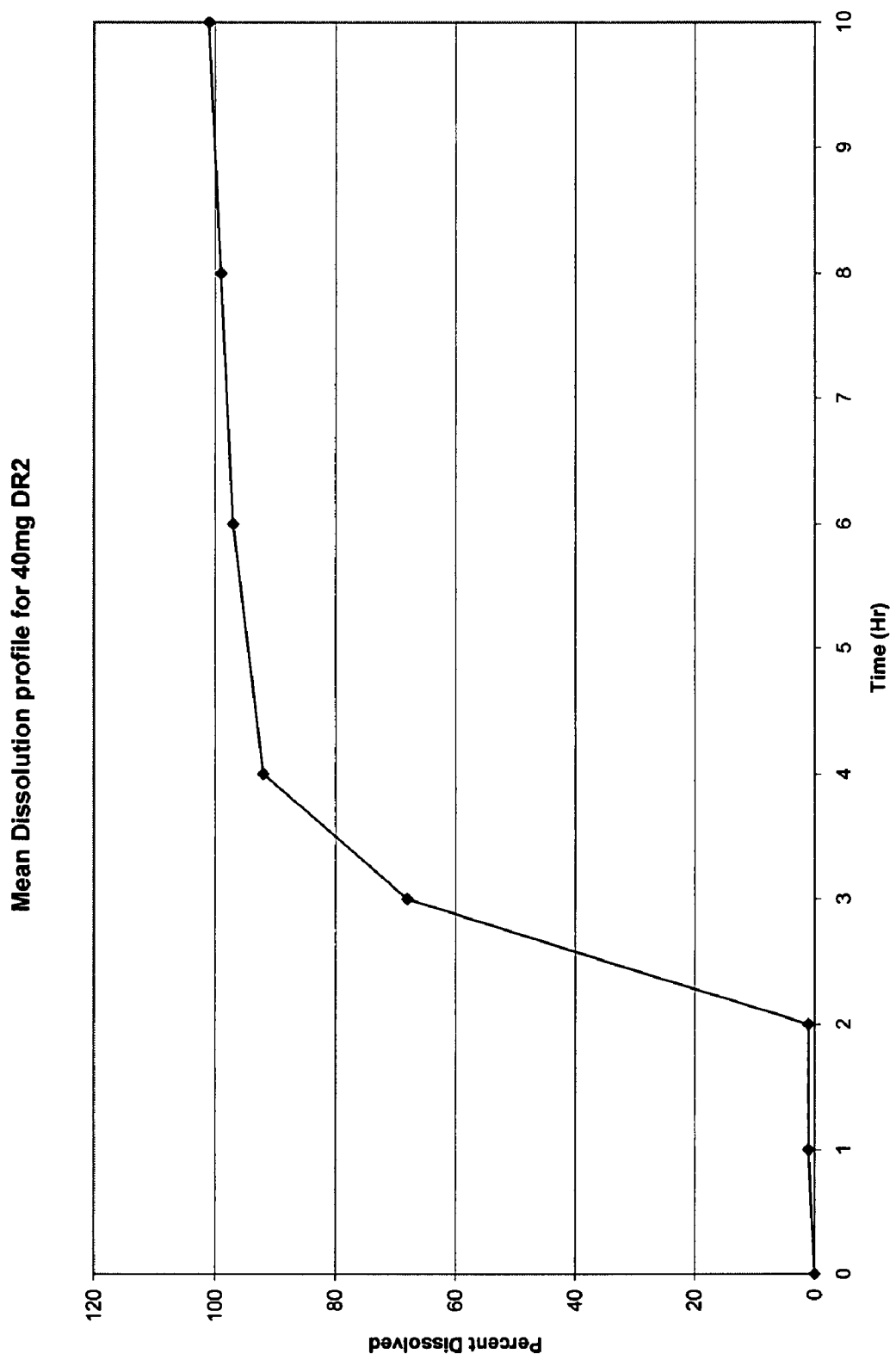
FIG. 7 shows the mean dissolution profile for 40 mg trospium chloride DR2 pellets.
Figure 8:
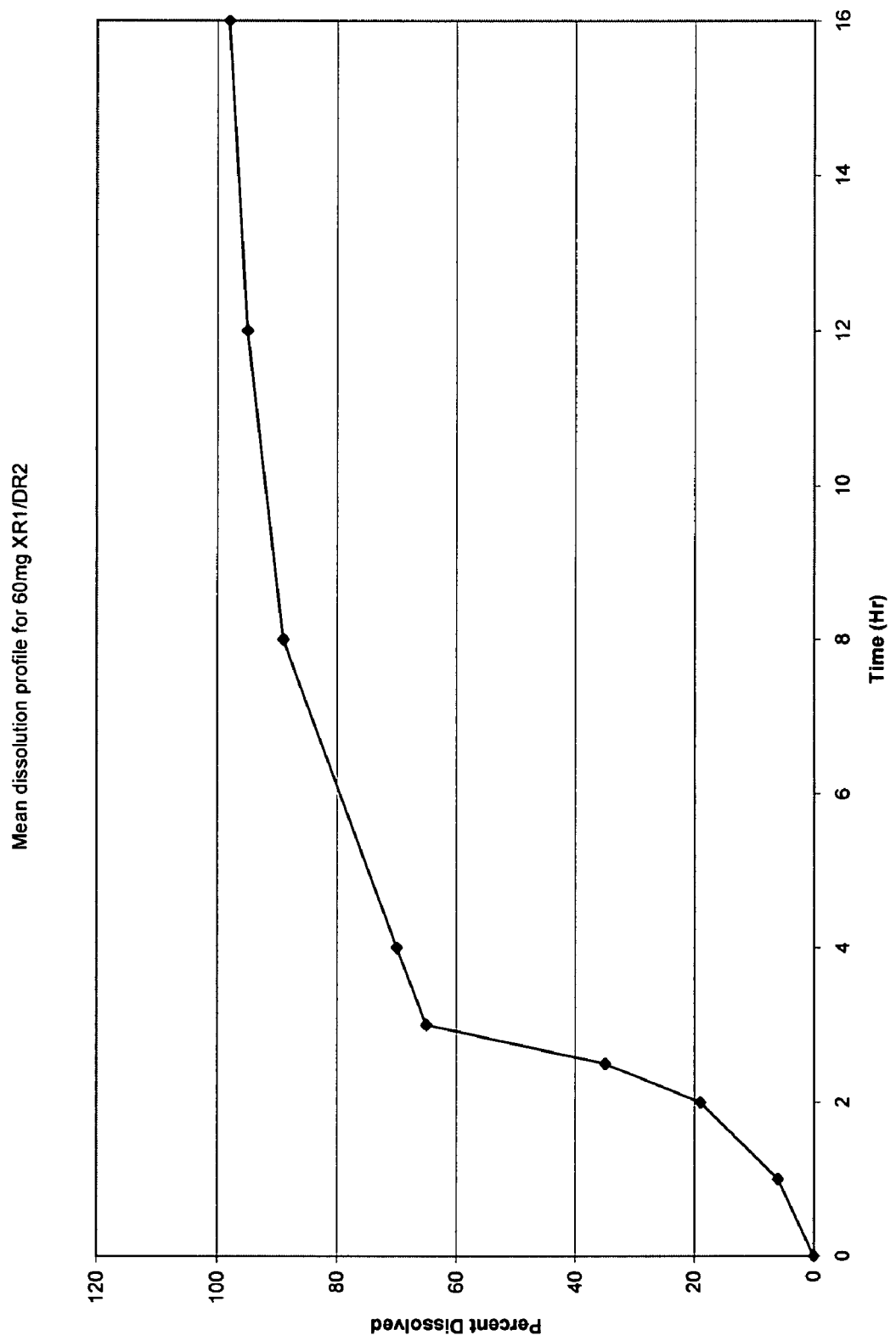
FIG. 8 shows the mean dissolution profile for 60 mg trospium chloride XR1/DR2 pellets.

The procedure followed to determine the dissolution profiles was:

FIG. 1: USP Apparatus II, 50 RPM. Media: 950 ml 0.1N HCl, pH 1.1;

FIG. 2: USP Apparatus II, 50 RPM. Media: 950 ml 50 mM phosphate buffer, pH 7.5;

FIG. 3: USP Apparatus II, 50 RPM. Media: 750 ml 0.1N HCl pH 1.1 for the first 2 Hrs and then media adjusted to pH 6.8 at 2 Hrs using phosphate buffer (total media volume=950 ml);

FIG. 4: USP Apparatus II, 50 RPM. Media: 950 ml 50 mM phosphate buffer, pH 7.5;

FIG. 5: USP Apparatus II, 50 RPM. Media: 950 ml 50 mM phosphate buffer, pH 7.5;

FIG. 6: USP Apparatus II, 50 RPM. Media: 750 ml 0.1N HCl pH 1.1 for the first 2 Hrs and then media adjusted to pH 6.8 at 2 Hrs using phosphate buffer (total media volume=950 ml);

FIG. 7 USP Apparatus II, 50 RPM. Media: 750 ml 0.1N HCl pH 1.1 for the first 2 Hrs and then media adjusted to pH 7.5 at 2 Hrs using phosphate buffer (total media volume=950 ml);

FIG. 8: USP Apparatus II, 50 RPM. Media: 750 ml 0.1N HCl pH 1.1 for the first 2 Hrs and then media adjusted to pH 7.5 at 2 Hrs using phosphate buffer (total media volume=950 ml).

FIG. 1 shows the dissolution profiles for the immediate release trospium chloride pellets in 0.1N HCl, pH 1.1. The profiles show a release greater than about 90% in about 15 minutes.

FIG. 2 shows the dissolution profiles for the extended release trospium chloride pellets in phosphate buffer, pH 6.8. The profiles show a release between about 25% and about 80% in about 4 hours, between about 50% and about 95% in about 8 hours, between about 70% and about 98% in about 12 hours and between about 90% and about 100% in 24 hours.

FIG. 3 shows the dissolution profiles for the delayed release trospium chloride pellets in 0.1N HCl and phosphate buffer, pH 6.8. The profiles show a release below 1% in acidic media and a release greater than about 90% in about 15 minutes after changing the pH FIG. 4 shows the mean dissolution profiles for the extended release 40 mg trospium chloride pellets in phosphate buffer, pH 6.8. The profiles show a release of less than 10% in about 2 hours, between about 20% and about 30% in about 4 hours, between about 50% and about 60% in about 8 hours, between about 70% and about 80% in about 12 hours and between about 90% and about 100% in 24 hours.

FIG. 5 shows the mean dissolution profiles for the extended release 50 mg trospium chloride pellets in phosphate buffer, pH 6.8. The profiles show a release of less than 10% in about 2 hours, between about 20% and about 30% in about 2 hours, between about 40% and about 60% in about 4 hours, between about 80% and about 90% in about 8 hours and between about 90% and about 100% in 12 hours.

FIG. 6 shows the mean dissolution profile for delayed release 35 mg trospium chloride pellets in 0.1N HCl and phosphate buffer, pH 6.8. The profiles show a release below 1% in acidic media and a release greater than about 40% in about 15 minutes after changing the pH, greater than 80% in 30 minute after changing the pH and greater than 90% within an hour after changing the pH.

FIG. 7 shows the mean dissolution profile for delayed release 40 mg trospium chloride pellets in 0.1N HCl and phosphate buffer, pH 6.8. The profiles show a release below 1% in acidic media and a release greater than about 30% in about 30 minutes after changing the pH, greater than 60% release in about 60 minutes after changing the pH and greater than 80% release within an hour after changing the pH and greater than 90% release within about 4 hour after changing the pH.

FIG. 8 shows the mean dissolution profile for extended release/delayed release 60 mg trospium chloride pellets in 0.1N HCl and phosphate buffer, pH 6.8. The profiles show a release between about 10% and about 20% during the first two hours in acidic media, and a release between 30% and 40% in about 30 minutes after changing the pH, between 60% and 70% release in about 1 hour after changing the pH, between 60% and 80% release in about 2 hours after changing the pH, between 70% and 80% release in about 4 hours after changing the pH, between 80% and 90% release in about 6 hours after changing the pH and greater than 90% release after a period of about 8 hours after changing the pH.

All the dissolution profiles are generated at 37° C.

TABLE 1a

Percent weight composition of trospium chloride dosage forms

| Components | IR Quantity per unit (mg) | IR % | DR1 Quantity per unit (mg) | DR1 % | DR2 Quantity per unit (mg) | DR2 % | XR1 Quantity per unit (mg) | XR1 % |
|---|---|---|---|---|---|---|---|---|
| Trospium Chloride | 40 | 13.64 | 40 | 9.13 | 40 | 9.23 | 40 | 11.97 |
| Sugar Spheres, NF | 152 | 51.84 | 152.1 | 34.71 | 152 | 35.07 | 152 | 45.48 |
| Hydroxypropyl methylcellulose, USP (Methocel ® E5 Premium LV) | 2 | 0.68 | 2 | 0.46 | 2 | 0.46 | 2 | 0.6 |
| Eudragit ® L30D-55 | N/A | N/A | 110.4 | 25.19 | N/A | N/A | N/A | N/A |
| Eudragit ® FS30D | N/A | N/A | N/A | N/A | 100 | 23.07 | N/A | N/A |
| Triethyl Citrate, NF | N/A | N/A | 16.6 | 3.79 | 5.6 | 1.29 | N/A | N/A |
| Opadry ® White, YS-1-7003 | 4 | 1.36 | 10.9 | 2.49 | 10.8 | 2.49 | 8.8 | 2.63 |
| Talc, USP | 2 | 0.68 | 13 | 2.97 | 29.8 | 6.88 | 2 | 0.6 |
| Ethyl Cellulose-based Coating Dispersion (Surelease ® Clear) | N/A | N/A | N/A | N/A | N/A | N/A | 36.2 | 10.83 |
| Hard Gelatin Capsules #0, White Opaque | 93.2 | 31.79 | 93.2 | 21.27 | 93.2 | 21.50 | 93.2 | 27.89 |
| Total | 293.2 | 100 | 438.2 | 100 | 433.4 | 100 | 334.2 | 100 |

TABLE 1b

Percent weight composition of trospium chloride dosage forms

| Component | 35 mg DR1 Capsules Quantity per unit (mg) | 35 mg DR1 Capsules % | 40 mg XR1-1 Capsules Quantity per unit (mg) | 40 mg XR1-1 Capsules % | 50 mg XR1-2 Capsules Quantity per unit (mg) | 50 mg XR1-2 Capsules % | 60 mg XR1:DR2 Capsules Quantity per unit (mg) | 60 mg XR1:DR2 Capsules % |
|---|---|---|---|---|---|---|---|---|
| Trospium Chloride | 35 | 9.13 | 40 | 11.07 | 50 | 11.17 | 60 | 11.09 |
| Sugar Spheres, NF | 133 | 34.71 | 152 | 42.06 | 190 | 42.46 | 228 | 42.16 |
| Hydroxypropyl methylcellulose, USP (METHOCEL ® E5 Premium LV) | 1.8 | 0.46 | 2 | 0.55 | 2.5 | 0.56 | 3 | 0.55 |
| EUDRAGIT ® L30D55 | 96.5 | 25.19 | N/A | N/A | N/A | N/A | N/A | N/A |
| EUDRAGIT ® FS30D | | | N/A | N/A | N/A | N/A | 75 | 13.87 |
| Triethyl Citrate, NF | 14.5 | 3.79 | N/A | N/A | N/A | N/A | 4.2 | 0.78 |
| OPADRY ® White, YS-1-7003 | 9.5 | 2.49 | 9.1 | 2.52 | 11.9 | 2.66 | 14.7 | 2.72 |
| Talc, USP | 11.4 | 2.97 | 2 | 0.55 | 2.5 | 0.56 | 23.8 | 4.4 |

TABLE 1b-continued

Percent weight composition of trospium chloride dosage forms

| Component | 35 mg DR1 Capsules Quantity per unit (mg) | % | 40 mg XR1-1 Capsules Quantity per unit (mg) | % | 50 mg XR1-2 Capsules Quantity per unit (mg) | % | 60 mg XR1:DR2 Capsules Quantity per unit (mg) | % |
|---|---|---|---|---|---|---|---|---|
| Ethyl Cellulose-based Coating Dispersion (SURELEASE ® Clear) | N/A | N/A | 51.3 | 14.19 | 85.6 | 19.13 | 27.1 | 5.01 |
| Hard Gelatin Capsules #0el, White Opaque | 105 | 21.27 | 105 | 29.05 | 105 | 23.46 | 105 | 19.42 |
| Total | 406.7 | 100 | 361.4 | 100 | 433.4 | 100 | 540.8 | 100 |

TABLE 2

Percent weight composition of trospium chloride pellets

| Components | IR % | DR1 % | DR2 % | XR1 % |
|---|---|---|---|---|
| Trospium Chloride | 20 | 11.59 | 11.76 | 16.6 |
| Sugar Spheres, NF | 76 | 44.09 | 44.68 | 63.08 |
| Hydroxypropyl methylcellulose, USP (METHOCEL ® E5 Premium LV) | 1 | 0.58 | 0.59 | 0.83 |
| EUDRAGIT ® L30D-55 | N/A | 32 | N/A | N/A |
| EUDRAGIT ® FS30D | N/A | N/A | 29.39 | N/A |
| Triethyl Citrate, NF | N/A | 4.81 | 1.65 | N/A |
| OPADRY ® White, YS-1-7003 | 2 | 3.16 | 3.17 | 3.66 |
| Talc, USP | 1 | 3.77 | 8.76 | 0.83 |
| Ethyl Cellulose-based Coating Dispersion (SURELEASE ® Clear) | N/A | N/A | N/A | 15 |
| Total | 100 | 100 | 100 | 100 |

TABLE 3

Coating process parameters

| Parameter | GPCG-1 |
|---|---|
| Inlet air temperature (° C.) | 50-55 |
| Product temperature (° C.) | 40-42 |
| Atomization air (bar) | 1.5 |
| Spray rate (g/min) | 8-12 |

Example 2

Trospium Chloride Extended Release Pellets

The composition of trospium chloride XR pellet filled capsules is provided in Table 1. Trospium chloride XR pellets were manufactured by coating trospium chloride immediate release pellets with a Surelease® Clear coating dispersion using a Glatt® fluid bed coater. Surelease® Clear is a 25% w/w aqueous dispersion supplied by Colorcon (West Point, Pa.). The Surelease® Clear coating dispersion was prepared by adding water to Surelease® Clear and mixing for 20 minutes to achieve a 20% w/w dispersion of Surelease® Clear. This 20% w/w Surelease® Clear dispersion was used for coating. The resulting dispersion was stirred throughout the coating process to prevent settling of coating components. Various coating levels of Surelease® Clear were examined with the objective of achieving extended release pellets with different extents of delay in coating dissolution, which are shown in Table 4. FIG. 2 shows the dissolution profiles for ethylcellulose coated trospium pellets.

TABLE 4

Composition of trospium chloride extended release pellets

| Material | 15% w/w Surelease | 20% w/w Surelease | 22.5% w/w Surelease | 25% w/w Surelease | 27.5% w/w Surelease | 30% w/w Surelease |
|---|---|---|---|---|---|---|
| Trospium chloride | 16.6 | 16.0 | 15.5 | 15.0 | 14.5 | 14.0 |
| Methocel E5 (HPMC) | 0.83 | 0.8 | 0.78 | 0.75 | 0.73 | 0.7 |
| Sugar Spheres NF 30/35 mesh | 63.08 | 60.8 | 58.9 | 57.0 | 55.1 | 53.2 |
| Altalc 300V (Talc USP) | 0.83 | 0.8 | 0.78 | 0.75 | 0.73 | 0.7 |

TABLE 4-continued

Composition of trospium chloride extended release pellets

| Material | 15% w/w Surelease | 20% w/w Surelease | 22.5% w/w Surelease | 25% w/w Surelease | 27.5% w/w Surelease | 30% w/w Surelease |
|---|---|---|---|---|---|---|
| Surelease Clear E-7-19010 | 15 | 20.0 | 22.5 | 25.0 | 27.5 | 30 |
| Opadry White YS-1-7003 | 3.66 | 1.6 | 1.55 | 1.5 | 1.45 | 1.4 |

Example 3

Trospium Chloride Delayed Release Pellets

The composition of trospium chloride DR pellet filled capsules is provided in Table 1. Table 2 provides the composition of delayed release pellets. Trospium chloride immediate release pellets were coated with Eudragit® L30D55 from a coating dispersion consisting of Eudragit® L30D55, triethylcitrate (a plasticizer), talc (an anti-tacking agent), and water using a Glatt® fluid bed coater. Eudragit® L30D55 is a 30% w/w aqueous dispersion supplied by Rohm America (Piscataway, N.J.). The Eudragit® L30D55 coating dispersion was prepared by dispersing talc in water and mixing for at least 20 minutes. Eudragit® L30D55 dispersion was sieved through an 80-mesh sieve. Triethylcitrate was added to the Eudragit®L30D55 dispersion and mixed for at least 30 minutes. The talc dispersion was then slowly poured into the Eudragit® L30D55/TEC dispersion and mixed for at least 30 minutes. The resulting dispersion (an 11.7% w/w Eudragit® L30D55 aqueous dispersion) was filtered through an 80-mesh sieve and stirred throughout the coating process to prevent settling of coating components. Various coating levels of Eudragit®L30D55 were examined with the objective of achieving an acid resistant coating. FIG. 3 shows the dissolution profiles for trospium chloride delayed release pellets.

Example 4

Combination XR/DR

Extended release pellets were prepared as in Example 2, with a 15% w/w coating of SURELEASE®. Delayed release pellets were manufactured by coating immediate release pellets with Eudragit FS30D, in a manner similar to Example 3. Eudragit®FS30D is a 30% aqueous dispersion supplied by Rohm America (Piscataway, N.J.). The Eudragit®FS30D coating dispersion is 18% w/w Eudragit®FS30D. The enteric coated pellets are combined with extended release pellets in the XR pellets to DR pellets ratio of 1:1, to achieve a total trospium chloride dose of 60 mg.

Example 5

Trospium Chloride Delayed Release at 35 mg Strength

Delayed release pellets manufactured by coating immediate release pellets with Eudragit® L30D55 as described in Example 3 were filled into capsules at a fill weight that provides 35 mg trospium chloride in the capsule dosage unit.

Example 6

Single Dose Human Pharmacokinetic Studies

A human trial of four controlled release formulations was conducted. The study compared four controlled release dosage units described in the previous examples (DR1 40 mg, DR2 40 mg, XR 40 mg and a mixture of 20 mg IR:120 mg DR2) with a 40 mg IR capsule given as once daily single dose and the 20 mg IR tablet (Spasmo-Lyt®, Madaus), which was given twice a day at 12 hour intervals.

Figure 9:
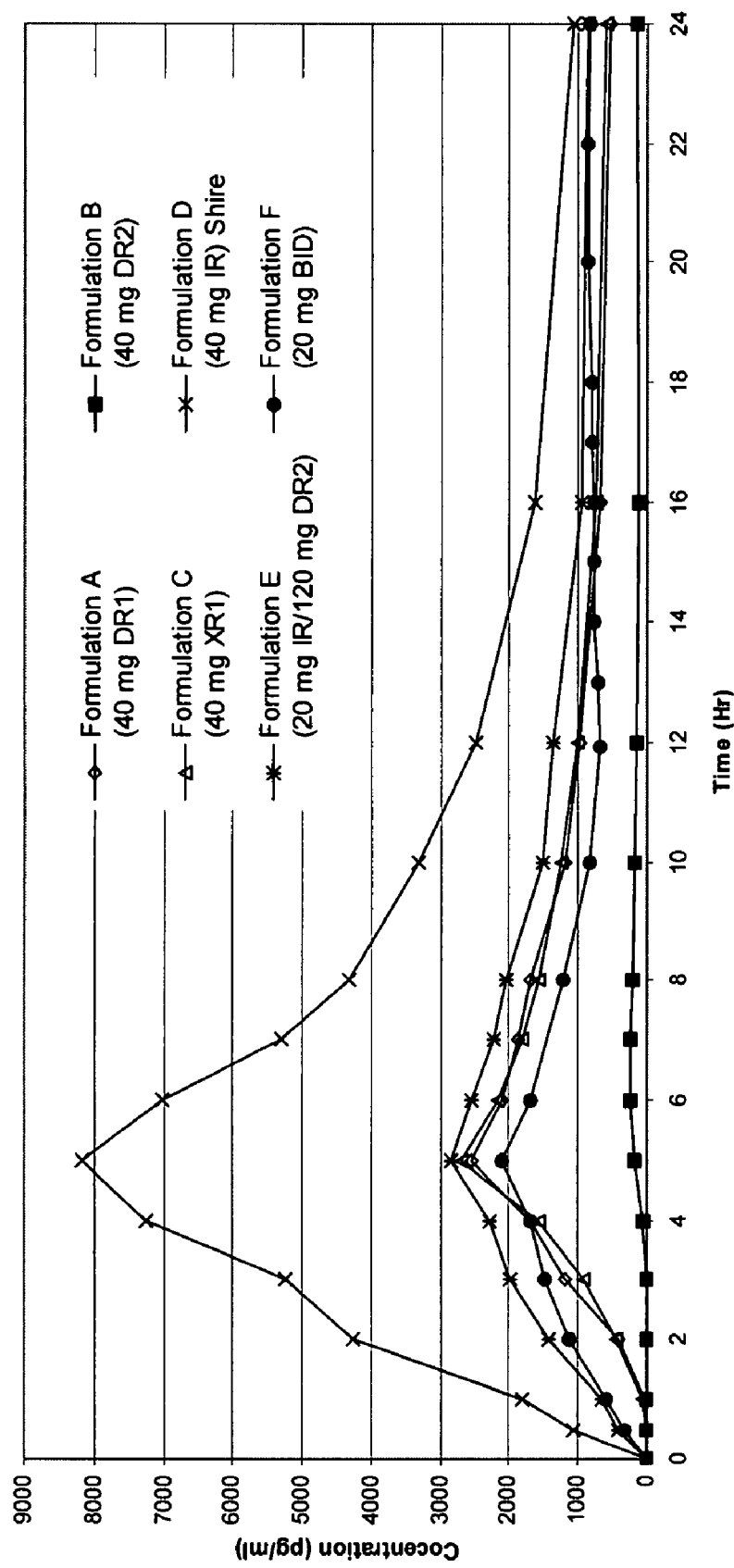
FIG. 9 shows the pharmacokinetic profiles of four exemplary controlled release compositions versus two immediate release products.
Figure 10:
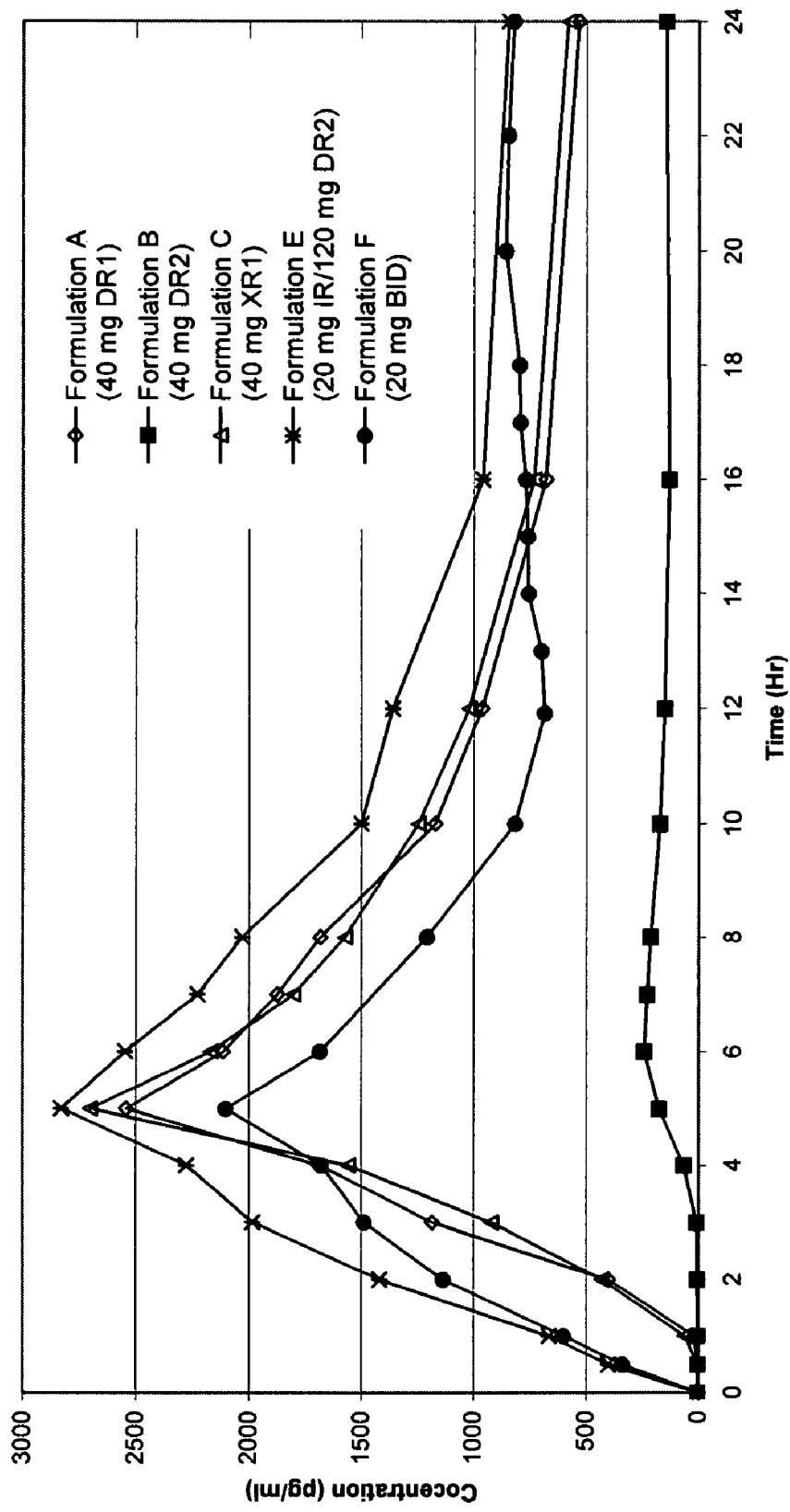
FIG. 10 shows the same data illustrated in FIG. 4 with Formulation D removed for ease of comparison.
Figure 11:
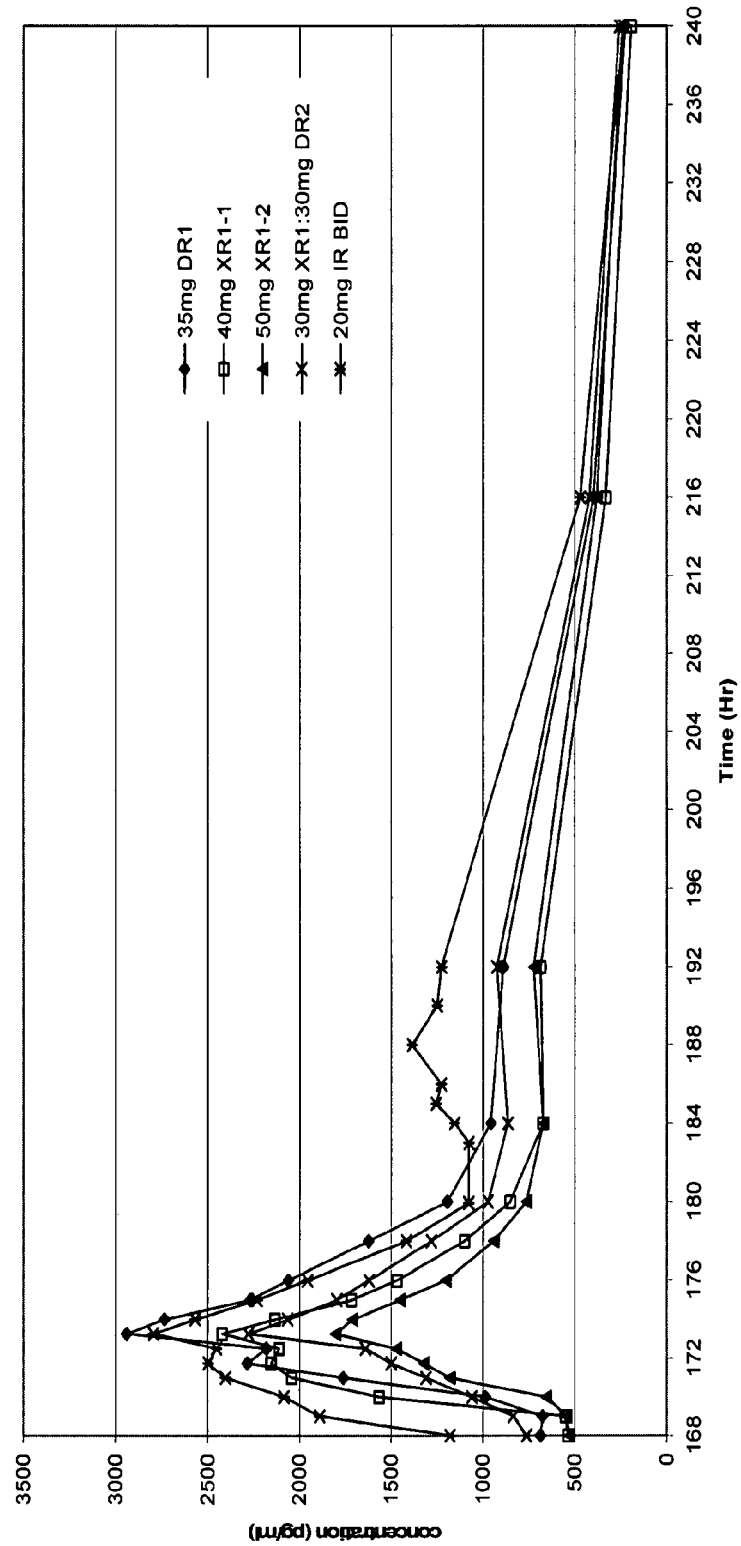
FIG. 11 shows the steady state pharmacokinetic profiles of four trospium chloride controlled release formulations.

FIG. 9 shows the pharmacokinetic profiles of the four once-a-day controlled release compositions versus the two immediate release products. FIG. 10 shows the same data with Formulation D removed for ease of comparisons. These data demonstrate that the DR1, XR1 and the combination of IR/DR2 produced pharmacokinetic profiles and parameters that are similar to the commercial IR twice a day product (FIGS. 9 and 10).

Table 5 presents single dose data on areas under the curve (AUC) over given time periods (0-24 hrs and 0-72 hrs) for immediate release product (20 mg bid) and controlled release products (40 mg DR1, 40 mg XR1 and 20 mg/120 mg IR/DR2 combination), including %F, which is a measure of bioequivalence. One can appreciate that at least the DR1 and XR controlled release products provide AUC data, which are comparable to those obtained with twice daily administered 20 mg immediate release trospium chloride.

TABLE 5

Single Dose Data for Various Trospium Chloride Formulations
Single Dose

| Formulation | AUC 0-24 (pg · hr/ml) | AUC 0-72 (pg · hr/ml) | % F |
|---|---|---|---|
| 20 mg bid | 23820 | 39831 | 100 |
| 40 mg DR1 | 23782 | 35589 | 89 |
| 40 mg XR | 24271 | 36098 | 91 |
| 20/120 mg IR/DR2 | 33244 | 52905 | 38 |

Example 7

Steady State Human Pharmacokinetic Studies

A second human trial was conducted comparing four controlled release formulations described in Table 1b with 20 mg IR tablet (Spasmo-Lyt®, Madaus), which was given twice a day at 12 hour intervals.

Table 6 presents steady state data on AUC (over a 72 hour time period), $C_{max}$, $C_{min}$, and %F obtained from the administration of the various trospium chloride formulations discussed in the preceding paragraph.

TABLE 6

Steady State Data for Various Trospium Chloride Formulations

| Time | A<br>35 mg DR1 | B<br>40 mg XR1-1 | C<br>50 mg XR1-2 | D<br>30 mg XR1:<br>30 mg DR2 | E Conc<br>20 mg IR<br>BID |
|---|---|---|---|---|---|
| Tmax (Hr) | 5.39 | 5.38 | 5.38 | 5.95 | 5.3 |
| Cmax (pg/mL) | 3164.9 | 2819.8 | 1908.7 | 2398.2 | 2978.9 |
| AUClast (Hr * pg/mL) | 55025.5 | 44972.1 | 42419.8 | 52060 | 67068.7 |
| AUCINF_obs (Hr * pg/mL) | 64076.8 | 53637.4 | 62784.5 | 63931.2 | 74294.4 |
| Relative BA (normalized) | 94% | 67% | 51% | 52% | 100% |

Example 8

Enteral Administration of a Trospium Chloride Pharmaceutical Composition

A delayed release formulation, according to the method of the invention, is prepared using a trospium salt, such as a fluoride, chloride, bromide or iodide, using a delayed release coating, which releases trospium at a pH of about 7.0. For example, an appropriate EUDRAGIT release controlling layer is selected so that the active ingredient is released at approximately neutral pH, which coincides substantially with the pH of the lower GI tract (e.g., lower intestine, colon, or both). Other release controlling layers may also be selected with the objective of providing a pharmaceutical composition comprising trospium as at least one active ingredient, which releases trospium in sections of the GI tract previously thought not to play a role in the delivery/absorption of significant amounts of trospium. See, e.g., Schroder, S. et al., in International Journal of Clinical Pharmacology and Therapeutics, Vol. 42-No. 10/2004 (543-549).

What is claimed is:

1. A method for treating a bladder dysfunction in a patient comprising orally administering to a patient suffering from a bladder dysfunction a once-a-day dosage formulation of a pharmaceutically acceptable salt of trospium ($Tr^+$) comprising at least one component selected from the group consisting of an extended release (XR) and a delayed release (DR) component;
    wherein at least a portion of said formulation releases trospium chloride in the lower gastrointestinal (GI) tract;
    which formulation provides an average Cmax at steady state of less than 2400 pg/ml of $Tr^+$ at a Tmax of less than 6 hours; and
wherein the bladder dysfunction is selected from the group consisting of urinary frequency, urgency, nocturia, urge-incontinence associated with detrusor instability, urge syndrome, and detrusor hyperreflexia.

2. The method of claim 1 in which the pharmaceutically acceptable salt of trospium is selected from the group consisting of a fluoride, chloride, bromide and iodide salt of trospium.

3. The method of claim 1 in which the pharmaceutically acceptable salt of trospium is trospium chloride.

4. The method of claim 1 which produces fewer incidents of one or more side effects, selected from the group of dry mouth, headache, constipation, dyspepsia, and abdominal pain, compared with the number of incidents of said one or more side effects observed after oral, twice daily administration of a 20 mg immediate release dosage formulation of trospium chloride.

5. The method of claim 1 in which said once-a-day formulation includes a mixture of a delayed release (DR) component and an extended release (XR) component.

6. The method of claim 5 in which the DR component and XR component each includes 30 mg of trospium chloride.

7. A method for treating a bladder dysfunction in a patient comprising orally administering to a patient suffering from a bladder dysfunction a once-a-day dosage formulation of a pharmaceutically acceptable salt of trospium ($Tr^+$), comprising at least one component selected from the group consisting of an extended release (XR) and a delayed release (DR) component,
    wherein at least a portion of said formulation releases trospium chloride in the lower gastrointestinal (GI) tract;
    which formulation provides an average Cmax at steady state of less than 2400 pg/ml of $Tr^+$ at a Tmax of less than 6 hours and which average steady state blood levels of $Tr^+$ do not fall below 500 pg/ml; and
    wherein the bladder dysfunction is selected from the group consisting of urinary frequency, urgency, nocturia, urge-incontinence associated with detrusor instability, urge syndrome, and detrusor hyperreflexia.

8. The method of claim 7 in which the pharmaceutically acceptable salt of trospium is selected from the group consisting of a fluoride, chloride, bromide and iodide salt of trospium.

9. The method of claim 7 in which the pharmaceutically acceptable salt of trospium is trospium chloride.

* * * * *